US007217522B2

(12) United States Patent
Brenner

(10) Patent No.: US 7,217,522 B2
(45) Date of Patent: May 15, 2007

(54) GENETIC ANALYSIS BY SEQUENCE-SPECIFIC SORTING

(75) Inventor: Sydney Brenner, Ely (GB)

(73) Assignee: Campass Genetics LLC, Lutherville, MD (US)

( * ) Notice: Subject to any disclaimer, the term of this patent is extended or adjusted under 35 U.S.C. 154(b) by 185 days.

(21) Appl. No.: 11/055,187

(22) Filed: Feb. 10, 2005

(65) Prior Publication Data

US 2005/0181408 A1    Aug. 18, 2005

Related U.S. Application Data

(60) Provisional application No. 60/543,887, filed on Feb. 12, 2004.

(51) Int. Cl.
*C12Q 1/68* (2006.01)
(52) U.S. Cl. .......................................... 435/6; 435/91.1
(58) Field of Classification Search .................... None
See application file for complete search history.

(56) References Cited

U.S. PATENT DOCUMENTS

| | | | |
|---|---|---|---|
| 4,321,365 A | 3/1982 | Wu et al. ................... | 536/24.2 |
| 5,093,245 A | 3/1992 | Keith et al. ................ | 435/91.2 |
| 5,102,785 A | 4/1992 | Livak et al. ................ | 435/6 |
| 5,149,625 A | 9/1992 | Church et al. .............. | 435/6 |
| 5,401,632 A | 3/1995 | Wang et al. ................ | 435/6 |
| 5,424,186 A | 6/1995 | Fodor et al. ................ | 435/6 |
| 5,445,934 A | 8/1995 | Fodor et al. ................ | 435/6 |
| 5,484,701 A | 1/1996 | Cocuzza et al. ............. | 435/6 |
| 5,503,980 A | 4/1996 | Cantor ....................... | 435/6 |
| 5,508,169 A | 4/1996 | Deugau et al. .............. | 435/6 |
| 5,599,675 A | 2/1997 | Brenner ...................... | 435/6 |
| 5,599,921 A | 2/1997 | Sorge et al. ................ | 536/24.33 |
| 5,631,134 A | 5/1997 | Cantor ....................... | 435/6 |
| 5,635,400 A | 6/1997 | Brenner ...................... | 435/320.1 |
| 5,695,934 A | 12/1997 | Brenner ...................... | 435/6 |
| 5,714,330 A | 2/1998 | Brenner et al. ............. | 435/6 |
| 5,744,305 A | 4/1998 | Fodor et al. ................ | 435/6 |
| 5,759,778 A | 6/1998 | Li et al. ..................... | 435/6 |
| 5,763,175 A | 6/1998 | Brenner ...................... | 435/6 |
| 5,846,719 A | 12/1998 | Brenner et al. ............. | 435/6 |
| 5,876,936 A * | 3/1999 | Ju ............................... | 435/6 |
| 5,916,810 A | 6/1999 | Jarvik ......................... | 435/440 |
| 5,935,793 A | 8/1999 | Wong .......................... | 435/6 |
| 6,007,987 A | 12/1999 | Cantor et al. ............... | 435/6 |
| 6,013,445 A | 1/2000 | Albrecht et al. ............. | 435/6 |
| 6,023,540 A | 2/2000 | Walt et al. .................. | 385/12 |
| 6,046,005 A | 4/2000 | Ju et al. ..................... | 435/6 |
| 6,054,270 A | 4/2000 | Southern .................... | 435/6 |
| 6,060,240 A | 5/2000 | Kamb et al. ................ | 435/6 |
| 6,060,596 A | 5/2000 | Lerner et al. ............... | 536/25.3 |
| 6,103,474 A | 8/2000 | Dellinger et al. ............ | 435/6 |
| 6,124,092 A | 9/2000 | O'Neill et al. .............. | 435/6 |
| 6,171,797 B1 | 1/2001 | Perbost et al. .............. | 435/6 |
| 6,261,782 B1 | 7/2001 | Lizardi et al. ............... | 435/6 |
| 6,280,950 B1 | 8/2001 | Lipshutz et al. ............. | 435/6 |
| 6,287,762 B1 | 9/2001 | Crouzet et al. .............. | 435/6 |
| 6,287,778 B1 | 9/2001 | Huang et al. ................ | 435/6 |
| 6,287,825 B1 | 9/2001 | Weissman et al. ........... | 435/6 |
| 6,323,043 B1 | 11/2001 | Caren et al. ................ | 436/518 |
| 6,348,313 B1 | 2/2002 | Sibson ........................ | 435/6 |
| 6,355,431 B1 | 3/2002 | Chee et al. .................. | 435/6 |
| 6,355,432 B1 | 3/2002 | Fodor et al. ................ | 435/6 |
| 6,383,754 B1 | 5/2002 | Kaufman et al. ............ | 435/6 |
| 6,440,667 B1 | 8/2002 | Fodor et al. ................ | 435/6 |
| 6,440,677 B2 | 8/2002 | Lipshutz et al. ............. | 435/6 |
| 6,458,530 B1 | 10/2002 | Morris et al. ............... | 435/6 |
| 6,468,749 B1 | 10/2002 | Ulanovsky et al. .......... | 435/6 |
| 6,514,699 B1 | 2/2003 | O'Neill et al. .............. | 435/6 |
| 6,544,739 B1 | 4/2003 | Fodor et al. ................ | 435/6 |
| 6,573,338 B2 | 6/2003 | Halverson et al. .......... | 525/375 |
| 6,677,121 B2 | 1/2004 | Lizardi et al. ............... | 435/6 |
| 6,773,886 B2 | 8/2004 | Kaufman et al. ............ | 435/6 |
| 6,958,225 B2 | 10/2005 | Dong .......................... | 435/91.2 |
| 2003/0003490 A1 | 1/2003 | Fan et al. .................... | 435/6 |
| 2003/0032020 A1 | 2/2003 | Brenner ...................... | 435/6 |
| 2003/0049616 A1 | 3/2003 | Brenner et al. ............. | 435/6 |

(Continued)

OTHER PUBLICATIONS

Delios et al. "Separation of complementary strands of plasmid DNA using the biotin-avidin system and its application to heteroduplex formation and RNA/DNA hybridizations in electron microscopy," Nucleic Acids Research, 13: 5457-5469 (1985).

Kandpal et al, "Selective enrichment of a large size genomic DNA fragment by affinity capture: an approach for genome mapping." Nucleic Acids Research, 18: 1789-1795f (1990).

Jordan et al. "Genome complexity reduction for SNP genotyping analysis," Proc. Natl. Acad. Sci., 99:2942-2947 (2002).

(Continued)

*Primary Examiner*—James Martinell
(74) *Attorney, Agent, or Firm*—Stephen C. Macevicz

(57) ABSTRACT

The invention provides methods for sorting polynucleotides from a population based on predetermined sequence characteristics. In one aspect, the method of the invention is carried out by extending a primer annealed polynucleotides having predetermined sequence characteristics to incorporate a predetermined terminator having a capture moiety, capturing polynucleotides having extended primers by a capture agent that specifically binds to the capture moiety, and melting the captured polynucleotides from the extended primers to form a subpopulation of polynucleotides having the predetermined sequence characteristics. In another aspect, the method of the invention is carried out on a population of tagged polynucleotides so that after a subpopulation is selected, the members of the subpopulation may be simultaneously analyzed using the unique tags on the polynucleotides to convey analytical information to a hybridization array for a readout.

8 Claims, 13 Drawing Sheets

U.S. PATENT DOCUMENTS

| | | | |
|---|---|---|---|
| 2003/0207300 A1 | 11/2003 | Matray et al. | 435/6 |
| 2003/0232348 A1 | 12/2003 | Jones et al. | 435/6 |
| 2004/0086914 A1 | 5/2004 | Cole et al. | 435/6 |
| 2004/0132056 A1 | 7/2004 | Su et al. | 435/6 |
| 2004/0259118 A1 | 12/2004 | Macevicz | 435/6 |
| 2005/0003558 A1 | 1/2005 | Zuckermann et al. | 436/518 |
| 2005/0095645 A1 | 5/2005 | Jones et al. | 435/6 |
| 2005/0142577 A1 | 6/2005 | Jones et al. | 435/6 |

OTHER PUBLICATIONS

Padgett and Sorge. "Creating seamless junctions independent of restriction sites in PCR cloning," Gene. 168: 31-35 (1996).

Brenner, et al, "In vitro cloning of complex mixtures of DNA on microbeads: Physical separation of differentially expressed cDNAs," Proc. Natl. Acad. Sci., 97: 1665-1670 (2000).

Brenner, et al, "Gene Expression Analysis by Massively Parallel Signature Sequencing (MPSS) On Microbead Arrays", Nature Biotechnology (2000) 18:630-634.

Czarnik, A. W., "Encoding Methods for Combinatorial Chemistry", Current Opinion in Chemical Biology (1997) 1:60-66.

Fan, et al, "Parallel Genotyping of Human SNPs Using Generic High-density Oligonucleotide Tag Arrays", Genome Research (2000) 10:853-860.

Fan, et al, "A Versatile Assay for High-Throughput Gene Expression Profiling on Universal Array Matrices", Genome Research (2004) 14:878-885.

Gerry, et al, "Universal DNA Microarray Method for Multiplex Detection of Low Abundance Point Mutations", J. Mol. Biol. (1999) 292:251-262.

Ju, "DNA sequencing with solid-phase-capturable dideoxynucleotides and energy transfer primers," Anal. Biochem., 309: 35-39 (2002).

Hirschhorn, et al, "SBE-TAGS: An Array-based Method for Efficient Single-Nucleotide Polymorphism Genotyping", Proc. Natl. Acad. Sci. (2000) 97:12164-12169.

Hughes, et al, "Expression Profiling Using Microarrays Fabricated by an Ink-jet Oligonucleotide Synthesizer", Nature Biotechnology (2001) 19:342-347.

Charnock-Jones et al, "Extension of incomplete cDNAs (ESTs) by biotin/streptavidin-mediated walking using the polymerase chain reaction," J. Biotechnology, 35: 205-215 (1994).

* cited by examiner

Combinatorial Tag With No "Commas"

Combinatorial Tag With "Commas" Between Words

Combinatorial Tag With "Commas" at Each End

Combinatorial Tag With "Commas-less" Property

|  |  |  |  |  | Melting Temperatue | | |
|---|---|---|---|---|---|---|---|
|  |  |  |  |  | Basic | Salt Adjusted | Nearest Neighbor |
| gtcta | tgtca | cttgt | tcitt | acaga | 53 | 61 | 52 |
|  |  |  |  |  |  |  |  |
| tgtca | tgtca | cttgt | tcitt | acaga | 53 | 61 | 54 |
| acaga | tgtca | cttgt | tcitt | acaga | 53 | 61 | 54 |
| cagaa | tgtca | cttgt | tcitt | acaga | 53 | 61 | 53 |
| aicat | tgtca | cttgt | tcitt | acaga | 51 | 59 | 52 |
| gaact | tgtca | cttgt | tcitt | acaga | 53 | 61 | 53 |
| cttgt | tgtca | cttgt | tcitt | acaga | 53 | 61 | 53 |
| tcitt | tgtca | cttgt | tcitt | acaga | 51 | 59 | 52 |
|  |  |  |  |  |  |  |  |
| gtcta | gtcta | cttgt | tcitt | acaga | 53 | 61 | 52 |
| gtcta | acaga | cttgt | tcitt | acaga | 53 | 61 | 52 |
| gtcta | cagaa | cttgt | tcitt | acaga | 53 | 61 | 52 |
| gtcta | aicat | cttgt | tcitt | acaga | 51 | 59 | 51 |
| gtcta | gaact | cttgt | tcitt | acaga | 53 | 61 | 53 |
| gtcta | cttgt | cttgt | tcitt | acaga | 53 | 61 | 52 |
| gtcta | tcitt | cttgt | tcitt | acaga | 51 | 59 | 51 |
|  |  |  |  |  |  |  |  |
| gtcta | tgtca | gtcta | tcitt | acaga | 53 | 61 | 52 |
| gtcta | tgtca | tgtca | tcitt | acaga | 53 | 61 | 52 |
| gtcta | tgtca | acaga | tcitt | acaga | 53 | 61 | 52 |
| gtcta | tgtca | cagaa | tcitt | acaga | 53 | 61 | 52 |
| gtcta | tgtca | aicat | tcitt | acaga | 51 | 59 | 51 |
| gtcta | tgtca | gaact | tcitt | acaga | 53 | 61 | 53 |
| gtcta | tgtca | tcitt | tcitt | acaga | 51 | 59 | 51 |
|  |  |  |  |  |  |  |  |
| gtcta | tgtca | cttgt | gtcta | acaga | 54 | 63 | 54 |
| gtcta | tgtca | cttgt | tgtca | acaga | 54 | 63 | 54 |
| gtcta | tgtca | cttgt | acaga | acaga | 54 | 63 | 54 |
| gtcta | tgtca | cttgt | cagaa | acaga | 54 | 63 | 54 |
| gtcta | tgtca | cttgt | aicat | acaga | 53 | 61 | 52 |
| gtcta | tgtca | cttgt | gaact | acaga | 54 | 63 | 54 |
| gtcta | tgtca | cttgt | cttgt | acaga | 54 | 63 | 54 |
|  |  |  |  | Mean | 53 | 61 | 53 |
|  |  |  |  | Std Dev | 1 | 1 | 1 |

Fig. 4

GENETIC ANALYSIS BY SEQUENCE-SPECIFIC SORTING

This application claims priority from U.S. provisional application Ser. No. 60/543,887 filed 12 Feb. 2004, which is incorporated herein by reference in its entirety.

FIELD OF THE INVENTION

The invention relates generally to methods and compositions for analyzing complex populations of polynucleotides, and more particularly, to methods and compositions for partitioning a population of polynucleotides into one or more subpopulations of lesser complexity.

BACKGROUND

A major goal in genetics research is to understand how sequence variations in the genome relate to complex traits, particularly susceptibilities for common diseases such as diabetes, cancer, hypertension, and the like, e.g. Collins et al, Nature, 422: 835–847 (2003). The draft sequence of the human genome has provided a highly useful reference for assessing variation, but it is only a first step towards understanding how the estimated 10 million or more common single nucleotide polymorphisms (SNPs), and other polymorphisms, such as inversions, deletions, insertions, and the like, determine or affect states of health and disease. Many powerful analytical approaches have been developed to address this problem, but none appear to have adequate throughput or flexibility for the types of studies required to associate traits practically and reliably with genomic variation, e.g. Syvanen, Nature Reviews Genetics, 2: 930–942 (2001). For example, it would be desirable to carry out trait-association studies in which a large set of genetic markers from populations of affected and unaffected individuals are compared. Such studies depend on the non-random segregation, or linkage disequilibrium, between the genetic markers and genes involved in the trait or disease being studied. Unfortunately, the extent and distribution of linkage disequilibrium between regions of the human genome is not well understood, but it is currently believed that successful trait-association studies in humans would require the measurement of 30–50,000 markers per individual in populations of at least 300–400 affected individuals and an equal number of controls, Kruglyak and Nickerson, Nature Genetics, 27: 234–236 (2001); Lai, Genome Research, 11: 927–929 (2001); Risch and Merikangas, Science, 273: 1516–1517 (1996); Cardon and Bell, Nature Reviews Genetics, 2: 91–99 (2001).

One approach to dealing with such whole-genome studies is to create subsets of genomic DNA having reduced complexity with respect to the genomes being analyzed in order to simplify the analysis, e.g. Lisitsyn et al, Science, 259: 946–951 (1993); Vos et al, Nucleic Acids Research, 23: 4407–4414 (1995); Dong et al, Genome Research, 11: 1418–1424 (2001); Jordan et al, Proc. Natl. Acad. Sci., 99: 2942–2947 (2002); Weissman et al, U.S. Pat. No. 6,506,562; Sibson, U.S. Pat. No. 5,728,524; Degau et al, U.S. Pat. No. 5,858,656. Unfortunately, most of these techniques rely on some form of subtraction, sequence destruction, or direct or indirect size selection to create subsets, which are difficult to implement and reduced sensitivity.

In view of the above, the field of genetic analysis would be advanced by the availability of a method for converting a highly complex population of DNA, such as a mixture of genomes, into subsets having reduced complexity without requiring subtraction, or other sequence destroying, steps.

SUMMARY OF THE INVENTION

The invention provides methods and compositions for sorting polynucleotides from a population based on predetermined sequence characteristics. In one aspect, the method of the invention is carried out by the following steps: (i) extending a primer annealed polynucleotides having predetermined sequence characteristics to incorporate a predetermined terminator having a capture moiety, (ii) capturing polynucleotides having extended primers by a capture agent that specifically binds to the capture moiety, and (iii) melting the captured polynucleotides from the extended primers to form a subpopulation of polynucleotides having the predetermined sequence characteristics.

In another aspect, the population of polynucleotides comprises fragments from a population of genomes, wherein the fragments from each genome has the same unique oligonucleotide tag attached. In this aspect, the invention includes a method of determining a frequency of a nucleotide at a predetermined locus in a population of genomes, such method comprising the following steps: (i) separately generating fragments of each genome of the population; (ii) attaching a unique oligonucleotide tag to each genome; (iii) selecting fragments from each genome that contains the predetermined locus; (iv) generating a labeled oligonucleotide tag from each unique oligonucleotide tag, the labeled oligonucleotide tag generating a signal indicative of the nucleotide at the predetermined locus; and (v) determining the frequency of the nucleotide at the predetermined locus by detecting the signals generated by the labeled oligonucleotide tags specifically hybridized with their respective tag complements, the respective tag complements being attached in spatially discrete regions on the one or more solid phase supports.

A composition comprising: a plurality of genomic fragments each from a same locus of a different genome and each having a different oligonucleotide tag attached. each oligonucleotide tag being selected from the same minimally cross-hybridizing set: and a solid phase support having a plurality of spatially discrete regions, each spatially discrete region having a tag complement from the minimally cross-hybridizing set covalently attached.

A method of determining a frequency of a nucleotide at a predetermined locus in a population of genomes, the method comprising the steps of: separately generating fragments of each genome of the population: attaching a unique oligonucleotide tag to each genome; selecting fragments from each genome that contains the predetermined locus; generating a labeled oligonucleotide tag from each unique oligonucleotide tag, the labeled oligonucleotide tag generating a signal indicative of the nucleotide at the predetermined locus; and determining the frequency of the nucleotide at the predetermined locus by detecting the signals generated by the labeled oligonucleotide tags specifically hybridized with their respective tag complements, the respective tag complements being attached in spatially discrete regions on the one or more solid phase supports.

BRIEF DESCRIPTION OF THE DRAWINGS

FIG. 4 lists melting temperatures of selected tags consisting of four words each having the comma-less property.

DEFINITIONS

Figure 1A:
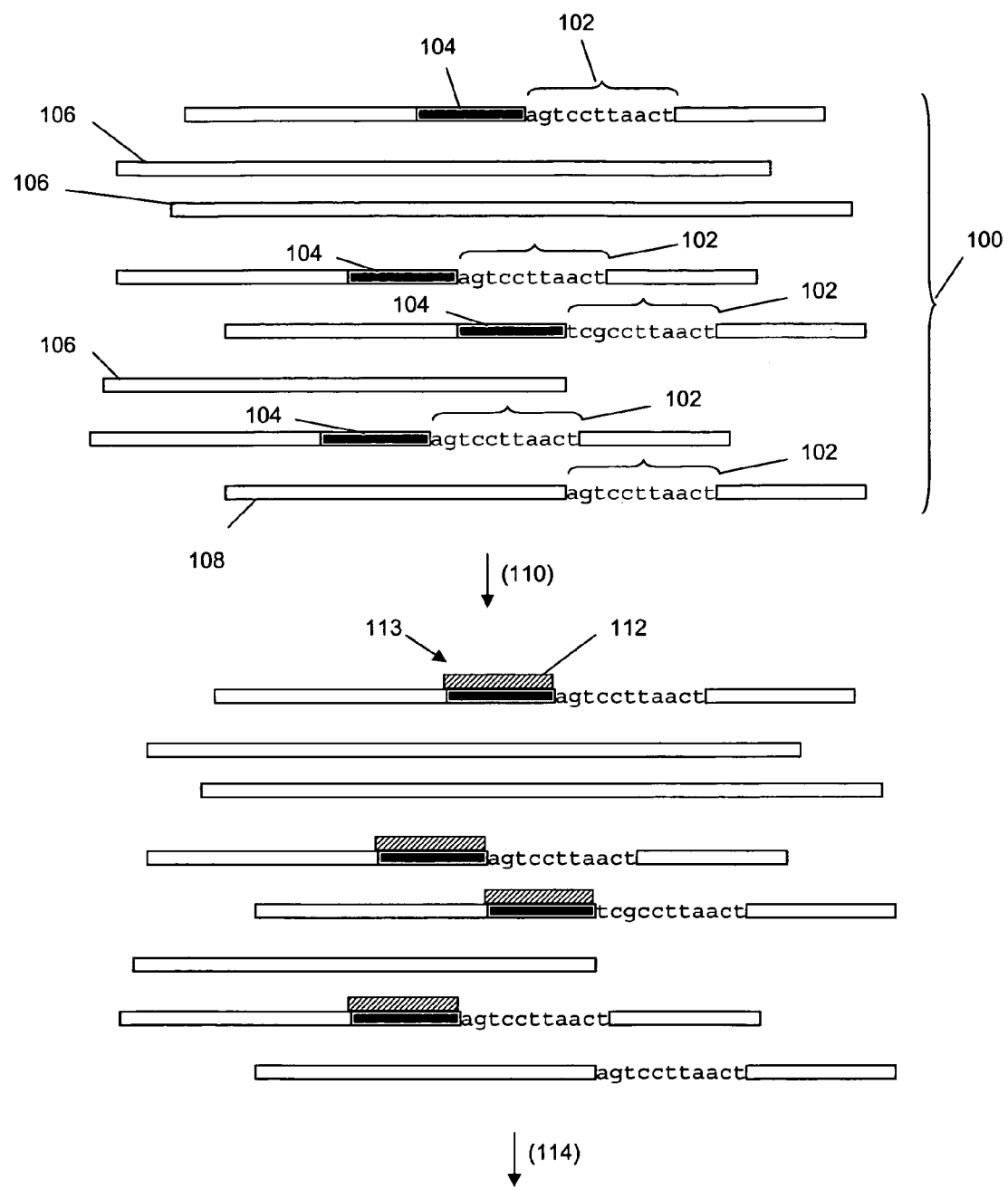
FIGS. 1A–1F illustrate the selection of particular fragments by common sequence elements.

"Addressable" in reference to tag complements means that the nucleotide sequence, or perhaps other physical or chemical characteristics, of a tag complement can be determined from its address, i.e. a one-to-one correspondence between the sequence or other property of the tag complement and a spatial location on, or characteristic of, the solid phase support to which it is attached. Preferably, an address of a tag complement is a spatial location, e.g. the planar coordinates of a particular region containing copies of the tag complement. However, tag complements may be addressed in other ways too, e.g. by microparticle size, shape, color, frequency of micro-transponder, or the like, e.g. Chandler et al, PCT publication WO 97/14028.

"Allele frequency" in reference to a genetic locus, a sequence marker, or the site of a nucleotide means the frequency of occurrence of a sequence or nucleotide at such genetic loci or the frequency of occurrence of such sequence marker, with respect to a population of individuals. In some contexts, an allele frequency may also refer to the frequency of sequences not identical to, or exactly complementary to, a reference sequence.

"Amplicon" means the product of an amplification reaction. That is, it is a population of polynucleotides, usually double stranded, that are replicated from one or more starting sequences. The one or more starting sequences may be one or more copies of the same sequence, or it may be a mixture of different sequences. Amplicons may be produced in a polymerase chain reaction (PCR), by replication in a cloning vector, or by linear amplification by an RNA polymerase, such as T7 or SP6, or by like techniques.

"Analyte" means any molecule, including organic, inorganic, or biomolecule, whose presence or absence or quantity or concentration in a sample is to be determined in an assay. In particular, biomolecule analytes include oligonucleotides, polynucleotides, genomic fragments, messenger RNAs (mRNAs), antibodies, enzymes, complementary DNAs (cDNAs), and like compounds.

"Complement" or "tag complement" as used herein in reference to oligonucleotide tags refers to an oligonucleotide to which an oligonucleotide tag specifically hybridizes to form a perfectly matched duplex or triplex. In embodiments where specific hybridization results in a triplex, the oligonucleotide tag may be selected to be either double stranded or single stranded. Thus, where triplexes are formed, the term "complement" is meant to encompass either a double stranded complement of a single stranded oligonucleotide tag or a single stranded complement of a double stranded oligonucleotide tag.

"Complexity" in reference to a population of double stranded or single stranded polynucleotides means the number of different species of polynucleotide present in the population. The related concept, "kinetic complexity" in reference to genomic DNA means the total number of basepairs present in non-repeating sequences, e.g. Wetmur, Critical Reviews in Biochemistry and Molecular Biology, 26: 227–259 (1991); Britten and Davidson, chapter 1 in Hames et al, editors, Nucleic Acid Hybridization: A Practical Approach (IRL Press, Oxford, 1985). For example, the following populations have the indicated sizes and complexities:

| Population | Population Size | Complexity |
|---|---|---|
| agtctactggtttca tcagatgaccaaagt (SEQ ID NO: 1) | 3 | 3 |
| gggttggggtttaccccttttagc cccaaccccaaatggggaaatcg (SEQ ID NO: 2) | | |
| tattagcttacttggcctta ataatcgaatgaaccggaat (SEQ ID NO: 3) | | |
| agtctactggtttcaattaattaatt tcagatgaccaaagttaattaattaa (SEQ ID NO: 4) | 2 | 2 |
| gggttggggtttaccccttttagc cccaaccccaaatggggaaatcg (SEQ ID NO: 2) | | |
| gggttggggtttaccccttttagc (SEQ ID NO: 5) | 5 | 3 |
| tcagatgaccaaagt (SEQ ID NO: 6) | | |
| tcagatgaccaaagt (SEQ ID NO: 6) | | |
| tcagatgaccaaagt (SEQ ID NO: 6) | | |
| tcagatgaccaaagttcagatgaccaaagt (SEQ ID NO: 7) | | |
| cccttagctg      agggct (SEQ ID NO: 8) | 8 | 3 |
| cccttagctg      agggct (SEQ ID NO: 8) | | |
| cccttagctg      agggct (SEQ ID NO: 8) | | |
| cccttagctg      agggctc (SEQ ID NO: 8) | | |

"Genetic locus," or "locus" in reference to a genome or target polynucleotide, means a contiguous subregion or segment of the genome or target polynucleotide. As used herein, genetic locus, or locus, may refer to the position of a gene or portion of a gene in a genome, or it may refer to any contiguous portion of genomic sequence whether or not it is within, or associated with, a gene. Preferably, a genetic locus refers to any portion of genomic sequence from a few tens of nucleotides, e.g. 10–30, in length to a few hundred nucleotides, e.g. 100–300, in length.

"Haplotype" means a series of alleles found at linked loci on a single chromosome. More particularly, haplotype means a series of single nucleotide polymorphisms at predetermined loci in a genomic DNA fragment.

"Ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically. As used herein, ligations are usually carried out enzymatically.

"Microarray" refers to a solid phase support, which may be planar or a collection of microparticles, that carries or carry oligo- or polynucleotides fixed or immobilized, usually covalently, at specific addressable locations. Preferably, a microarray is a solid phase support having a planar surface, which carries an array of nucleic acids, each member of the array comprising identical copies of an oligonucleotide or polynucleotide immobilized to a fixed region, which does not overlap with those of other members of the array. Typically, the oligonucleotides or polynucleotides are single stranded and are covalently attached to the solid phase support at known, determinable, or addressable, locations. The density of non-overlapping regions containing nucleic acids in a microarray is typically greater than 100 per $cm^2$, and more preferably, greater than 1000 per $cm^2$. Microarray technology is reviewed in the following references: Schena, Editor, Microarrays: A Practical Approach (IRL Press, Oxford, 2000); Southern, Current Opin. Chem. Biol., 2: 404–410 (1998); Nature Genetics Supplement, 21: 1–60 (1999).

"Nucleoside" as used herein includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543–584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al, Exp. Opin. Ther. Patents, 6: 855–870 (1996); Mesmaeker et al, Current Opinion in Structual Biology, 5: 343–355 (1995); and the like. Exemplary types of polynucleotides that are capable of enhancing duplex stability include oligonucleotide N3'→P5' phosphoramidates (referred to herein as "amidates"), peptide nucleic acids (referred to herein as "PNAs"), oligo-2'-O-alkylribonucleotides, polynucleotides containing C-5 propynylpyrimidines, and like compounds. Such oligonucleotides are either available commercially or may be synthesized using methods described in the literature.

"Perfectly matched" in reference to a duplex means that the poly- or oligonucleotide strands making up the duplex form a double stranded structure with one other such that every nucleotide in each strand undergoes Watson-Crick basepairing with a nucleotide in the other strand. The term also comprehends the pairing of nucleoside analogs, such as deoxyinosine, nucleosides with 2-aminopurine bases, and the like, that may be employed. In reference to a triplex, the term means that the triplex consists of a perfectly matched duplex and a third strand in which every nucleotide undergoes Hoogsteen or reverse Hoogsteen association with a basepair of the perfectly matched duplex. Conversely, a "mismatch" in a duplex between a tag and an oligonucleotide means that a pair or triplet of nucleotides in the duplex or triplex fails to undergo Watson-Crick and/or Hoogsteen and/or reverse Hoogsteen bonding.

"Polynucleotide" or "oligonucleotide" are used interchangeably and each mean a linear polymer of natural or modified nucleotide monomers. Monomers making up polynucleotides and oligonucleotides include deoxyribonucleotides, ribonucleotides, 2'-deoxy-3'-phosphorothioate nucleosides, peptide nucleic acids (PNAs), and the like, that are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Polynucleotides typically range in size from a few monomeric units, e.g. 5–40, when they are usually referred to as "oligonucleotides," to several thousand monomeric units. Whenever a polynucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA) linked by phosphodiester linkages; however, they may also comprise non-natural nucleotide analogs, e.g. including modified bases, sugars, or internucleosidic linkages. It is clear to those skilled in the art when oligonucleotides having natural or non-natural nucleotides may be employed, e.g. where processing by enzymes is called for, usually polynucleotides consisting solely of natural nucleotides are required. Likewise, where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of from 14 to 36 nucleotides.

"Readout" means a parameter, or parameters, which are measured and/or detected that can be converted to a number or value. In some contexts, readout may refer to an actual numerical representation of such collected or recorded data. For example, a readout of fluorescent intensity signals from a microarray is the address and fluorescence intensity of a signal being generated at each hybridization site of the microarray; thus, such a readout may be registered or stored in various ways, for example, as an image of the microarray, as a table of numbers, or the like.

"Sequence determination" or "determining a nucleotide sequence" in reference to polynucleotides includes determination of partial as well as full sequence information of the polynucleotide. That is, the term includes sequence comparisons, fingerprinting, and like levels of information about a target polynucleotide, as well as the express identification and ordering of nucleosides, usually each nucleoside, in a target polynucleotide. The term also includes the determination of the identity, ordering, and locations of one, two, or three of the four types of nucleotides within a target polynucleotide. For example, in some embodiments sequence determination may be effected by identifying the ordering and locations of a single type of nucleotide, e.g. cytosines, within the target polynucleotide "CATCGC . . . " so that its sequence is represented as a binary code, e.g. "100101..." for "C-(not C)-(not C)-C-(not C)-C..." and the like.

"Signature sequence" means a sequence of nucleotides derived from a polynucleotide such that the ordering of nucleotides in the signature is the same as their ordering in the polynucleotide and the sequence contains sufficient information to identify the polynucleotide in a population. Signature sequences may consist of a segment of consecutive nucleotides (such as, (a,c,g,t,c) of the polynucleotide "acgtcggaaatc"(SEQ ID NO: 23)), or it may consist of a sequence of every second nucleotide (such as, (c,t,g,a,a,) of the polynucleotide "acgtcggaaatc"(SEQ ID NO: 23)), or it may consist of a sequence of nucleotide changes (such as, (a,c,g,t,c,g,a,t,c) of the polynucleotide "acgtcggaaatc"(SEQ ID NO: 23)), or like sequences.

"Specific" or "specificity" in reference to the binding of one molecule to another molecule, such as a binding compound, or probe, for a target analyte, means the recognition, contact, and formation of a stable complex between the probe and target, together with substantially less recognition, contact, or complex formation of the probe with other molecules. In one aspect, "specific" in reference to the binding of a first molecule to a second molecule means that to the extent the first molecule recognizes and forms a complex with another molecules in a reaction or sample, it forms the largest number of the complexes with the second molecule. In one aspect, this largest number is at least fifty percent of all such complexes form by the first molecule. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, ionic and hydrophobic interactions, and the like, dominate the interaction of the molecules. As used herein, "stable complex" in reference to two or more molecules means that such molecules form noncovalently linked aggregates, e.g. by specific binding, that under assay conditions are thermodynamically more favorable than a non-aggregated state.

"Spectrally resolvable" in reference to a plurality of fluorescent labels means that the fluorescent emission bands of the labels are sufficiently distinct, i.e. sufficiently non-overlapping, that molecular tags to which the respective labels are attached can be distinguished on the basis of the fluorescent signal generated by the respective labels by standard photodetection systems, e.g. employing a system of band pass filters and photomultiplier tubes, or the like, as exemplified by the systems described in U.S. Pat. Nos. 4,230,558; 4,811,218, or the like, or in Wheeless et al, pgs. 21–76, in Flow Cytometry: Instrumentation and Data Analysis (Academic Press, New York, 1985).

"Terminator" means a nucleotide that can be incorporated into a primer by a polymerase extension reaction, wherein the nucleotide prevents subsequent incorporation of nucleotides to the primer and thereby halts polymerase-mediated extension. Typical terminators are nucleoside triphosphates that lack a 3'-hydroxyl substituent and include 2',3'-dideoxyribose, 2',3'-didehydroribose, and 2',3'-dideoxy-3'-haloribose, e.g. 3'-deoxy-3'-fluoro-ribose or 2',3'-dideoxy-3'-fluororibose nucleosides, for example. Alternatively, a ribofuranose analog can be used in terminators, such as 2',3'-dideoxy-β-D-ribofuranosyl, β-D-arabinofuranosyl, 3'-deoxy-β-D-arabinofuranosyl, 3'-amino-2',3'-dideoxy-β-D-ribofaranosyl, and 2,3'-dideoxy-3'-fluoro-β-D-ribofuranosyl. A variety of terminators are disclosed in the following references: Chidgeavadze et al., Nucleic Acids Res., 12: 1671–1686 (1984); Chidgeavadze et al., FEBS Lett., 183: 275–278 (1985); Izuta et al, Nucleosides & Nucleotides, 15: 683–692 (1996); and Krayevsky et al, Nucleosides & Nucleotides, 7: 613–617 (1988). Nucleotide terminators also include reversible nucleotide terminators, e.g. Metzker et al. Nucleic Acids Res., 22(20):4259 (1994). Terminators of particular interest are terminators having a capture moiety, such as biotin, or a derivative thereof, e.g. Ju, U.S. Pat. No. 5,876,936, which is incorporated herein by reference. As used herein, a "predetermined terminator" is a terminator that basepairs with a pre-selected nucleotide of a template.

"Uniform" in reference to spacing or distribution means that a spacing between objects, such as sequence markers, or events may be approximated by an exponential random variable, e.g. Ross, Introduction to Probability Models, $7^{th}$ edition (Academic Press, New York, 2000). In regard to spacing of sequence markers in a mammalian genome, it is understood that there are significant regions of repetitive sequence DNA in which a random sequence model of the genomic DNA does not hold. "Uniform" in reference to spacing of sequence markers preferably refers to spacing in uniques sequence regions, i.e. non-repetitive sequence regions, of a genome.

DETAILED DESCRIPTION OF THE INVENTION

The invention provides methods for sorting polynucleotides based on predetermined sequence characteristics to form subpopulations of reduced complexity. In one aspect, such sorting methods are used to analyze populations of uniquely tagged polynucleotides, such as genome fragments. During or at the conclusion of repeated steps of sorting in accordance with the invention, the tags may be replicated, labeled and hybridized to a solid phase support, such as a microarray, to provide a simultaneous readout of sequence information from the polynucleotides. As described more fully below, predetermined sequence characteristics include, but are not limited to, a unique sequence region at a particular locus, a series of single nucleotide polymorphisms (SNPs) at a series of loci, or the like. In one aspect, such sorting of uniquely tagged polynucleotides allows massively parallel operations, such as simultaneously sequencing, genotyping, or haplotyping many thousands of genomic DNA fragments from different genomes.

Figure 1B:
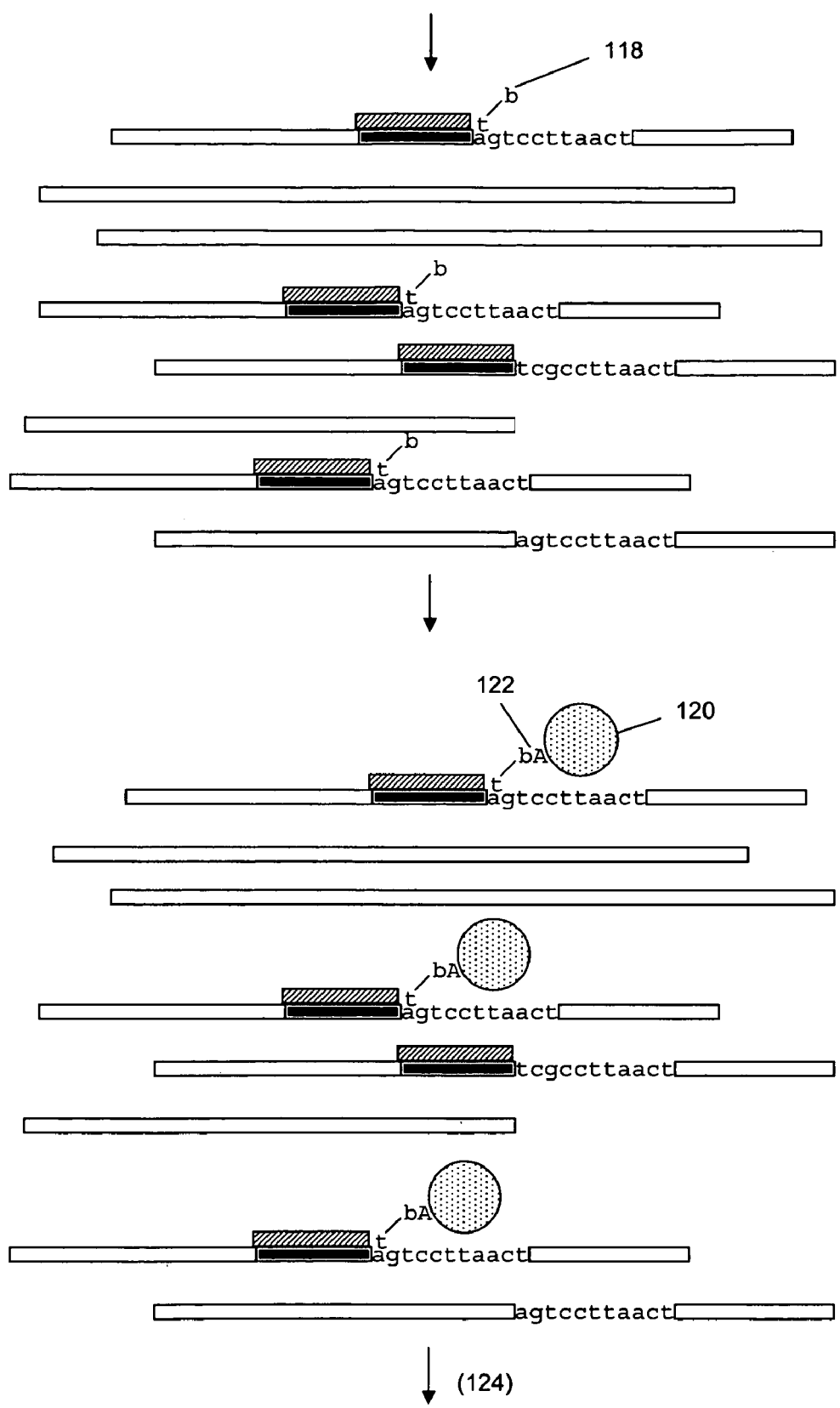
Figure 1C:
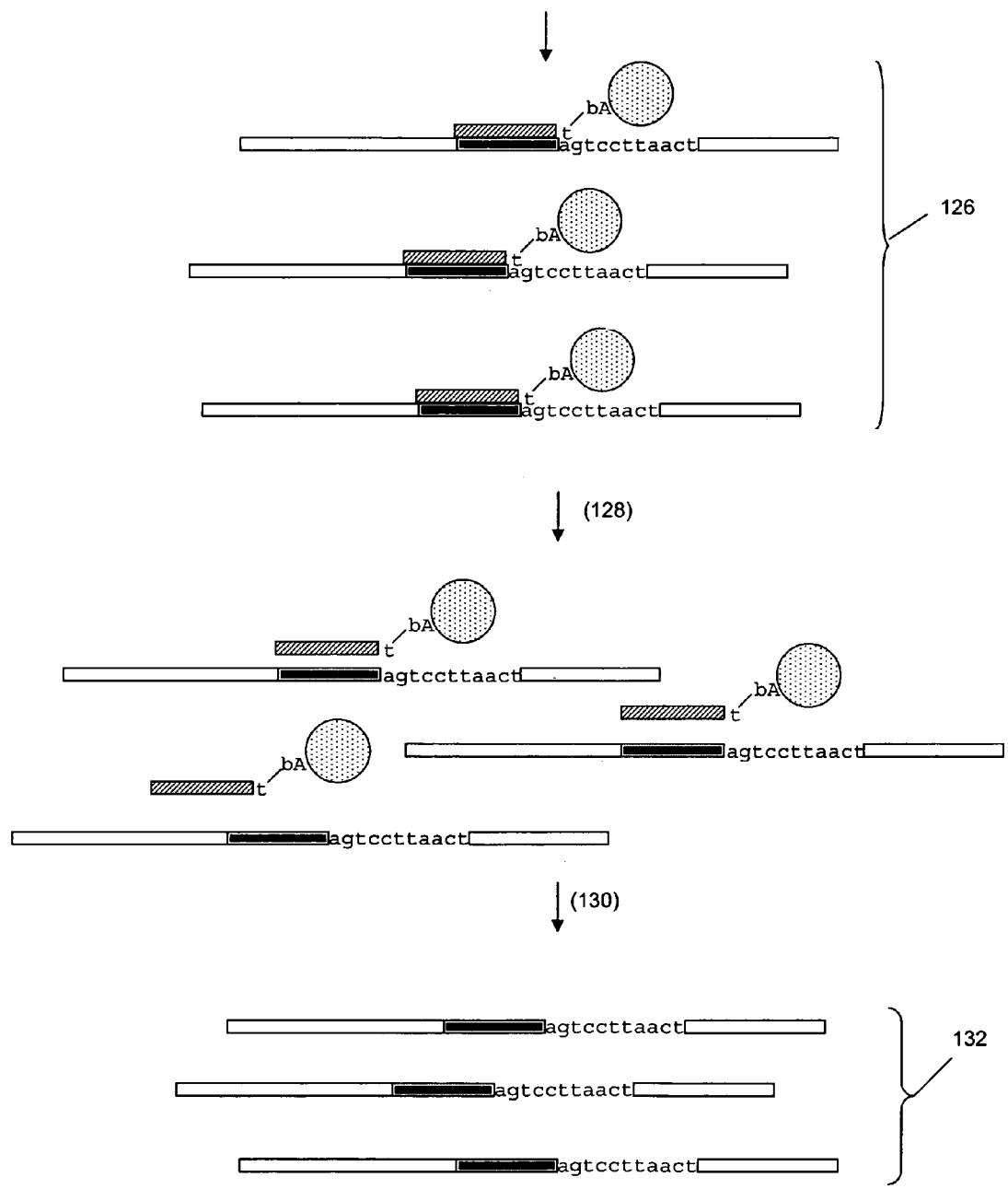

One aspect of the complexity-reducing method of the invention is illustrated in FIGS. 1A–1C. Population of polynucleotides (100), sometimes referred to herein as a parent population, includes sequences having a known sequence region that may be used as a primer binding site (104) that is immediately adjacent to (and upstream of) a region (102)(SEQ ID NO: 24 or SEQ ID NO: 25) that may contain one or more SNPs. Primer binding site (104) has the same, or substantially the same, sequence whenever it is present. That is, there may be differences in the sequences among the primer binding sites (104) in a population, but the primer selected for the site must anneal and be extended by the extension method employed, e.g. DNA polymerase extension. Primer binding site (104) is an example of a predetermined sequence characteristic of polynucleotides in population (100). Parent population (100) also contains polynucleotides (106) that do not contain either a primer binding site (104) or polymorphic region (102) and polynucleotides (108) that do not contain a primer binding site (104). but do contain polymorphic region (102). In one aspect, the invention provides a method for isolating sequences from population (100) that have primer binding sites (104) and polymorphic regions (102). This is accomplished by annealing (110) primers (112) to polynucleotides having primer binding sites (104) to form primer-polynucleotide duplexes (113). After primers (112 ) are annealed, they are extended (114) to incorporate a predetermined terminator having a capture moiety. Extension may be effected by polymerase activity, chemical or enzymatic ligation, or combinations of both. A terminator is incorporated so that successive incorporations (or at least uncontrolled successive incorporations) are prevented.

This step of extension may also be referred to as "template-dependent extension" to mean a process of extending a primer on a template nucleic acid that produces an extension product, i.e. an oligonucleotide that comprises the primer plus one or more nucleotides, that is complementary to the template nucleic acid. As noted above, template-dependent extension may be carried out several ways, including chemical ligation, enzymatic ligation, enzymatic polymerization, or the like. Enzymatic extensions are preferred because the requirement for enzymatic recognition increases the specificity of the reaction. In one aspect, such extension is carried out using a polymerase in conventional reaction, wherein a DNA polymerase extends primer (112) in the presence of at least one terminator labeled with a capture moiety. Depending on the embodiment, there may be from one to four terminators (so that synthesis is terminated at any one or at all or at any subset of the four natural nucleotides). For example, if only a single capture moiety is employed, e.g. biotin, extension may take place in four separate reactions, wherein each reaction has a different terminator, e.g. biotinylated dideoxyadenosine triphosphate, biotinylated dideoxycytidine triphosphate, and so on. On the other hand, if four different capture moieties are employed, then four terminators may be used in a single reaction. Preferably, the terminators are dideoxynucleoside triphosphates. Such terminators are available with several different capture moieties, e.g. biotin, fluorescein, dinitrophenol, digoxigenin, and the like (Perkin Elmer Lifesciences). Preferably, the terminators employed are biotinylated dideoxynucleoside triphosphates (biotin-ddNTPs), whose use in sequencing reactions is described by Ju et al, U.S. Pat. No. 5,876,936, which is incorporated by reference. In one aspect of the invention, four separate reactions are carried out, each reaction employing only one of the four terminators, biotin-ddATP, biotin-ddCTP, biotin-ddGTP, or biotin-ddTTP. In further preference, in such reactions, the ddNTPs without capture moieties are also included to minimize misincorporation.

As illustrated in FIG. 1B, primer (112) is extended to incorporate a biotinylated dideoxythymidine (118), after which primer-polynucleotide duplexes having the incorporated biotins are captured with a capture agent, which in this illustration is an avidinated (122) (or streptavidinated) solid support, such as a microbead (120). Captured polynucleotides (126) are separated (124) and polynucleotides are melted (128) from the extended primers to form (130) population (132) that has a lower complexity than that of the parent population (100). Other capture agents include antibodies, especially monoclonal antibodies, that form specific and strong complexes with capture moieties. Many such antibodies are commercially available that specifically bind to biotin, fluorescein, dinitrophenol, digoxigenin, rhodamine, and the like (e.g. Molecular Probes, Eugene, Oreg.).

Figure 1D:
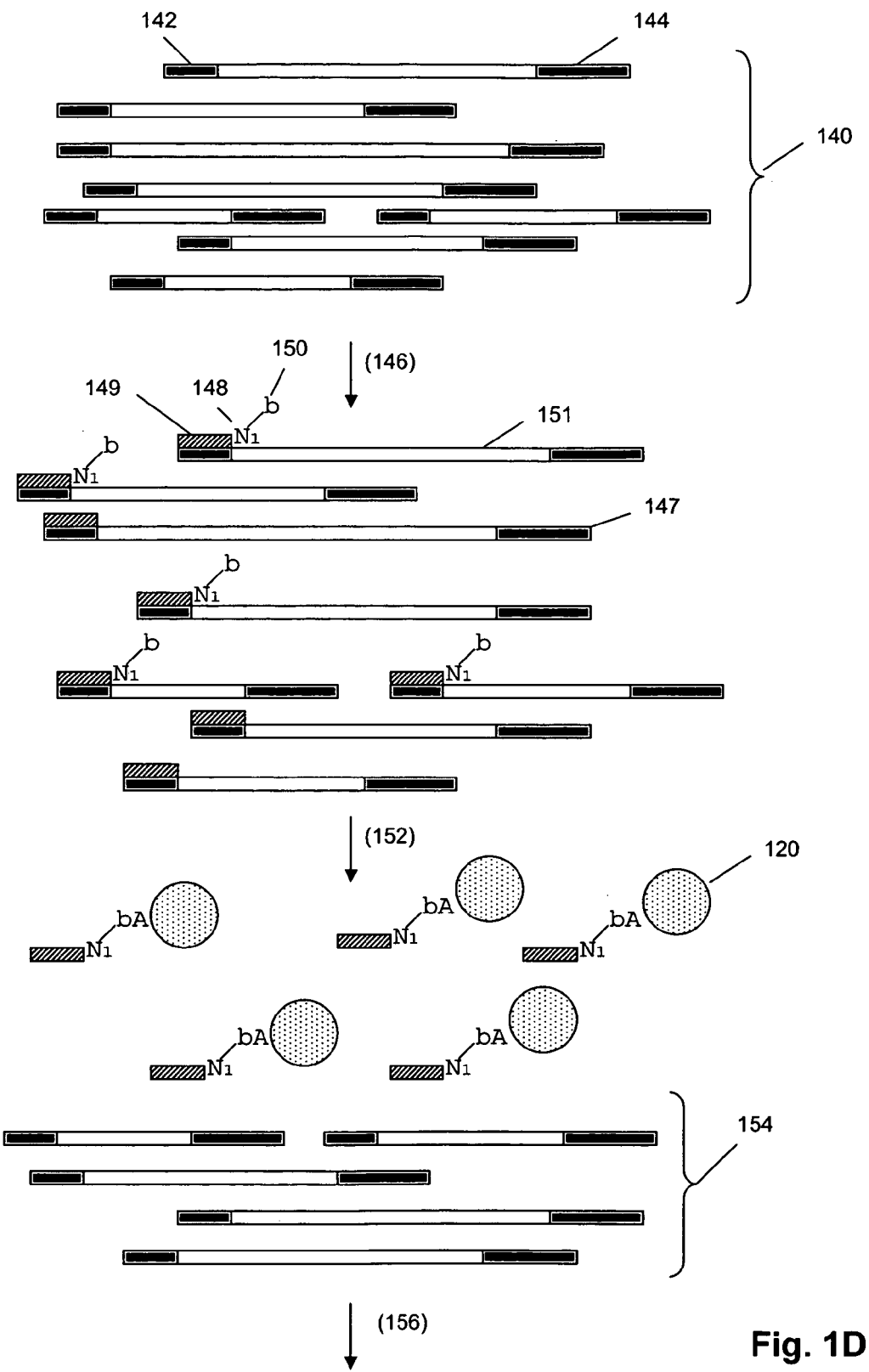
Figure 1E:
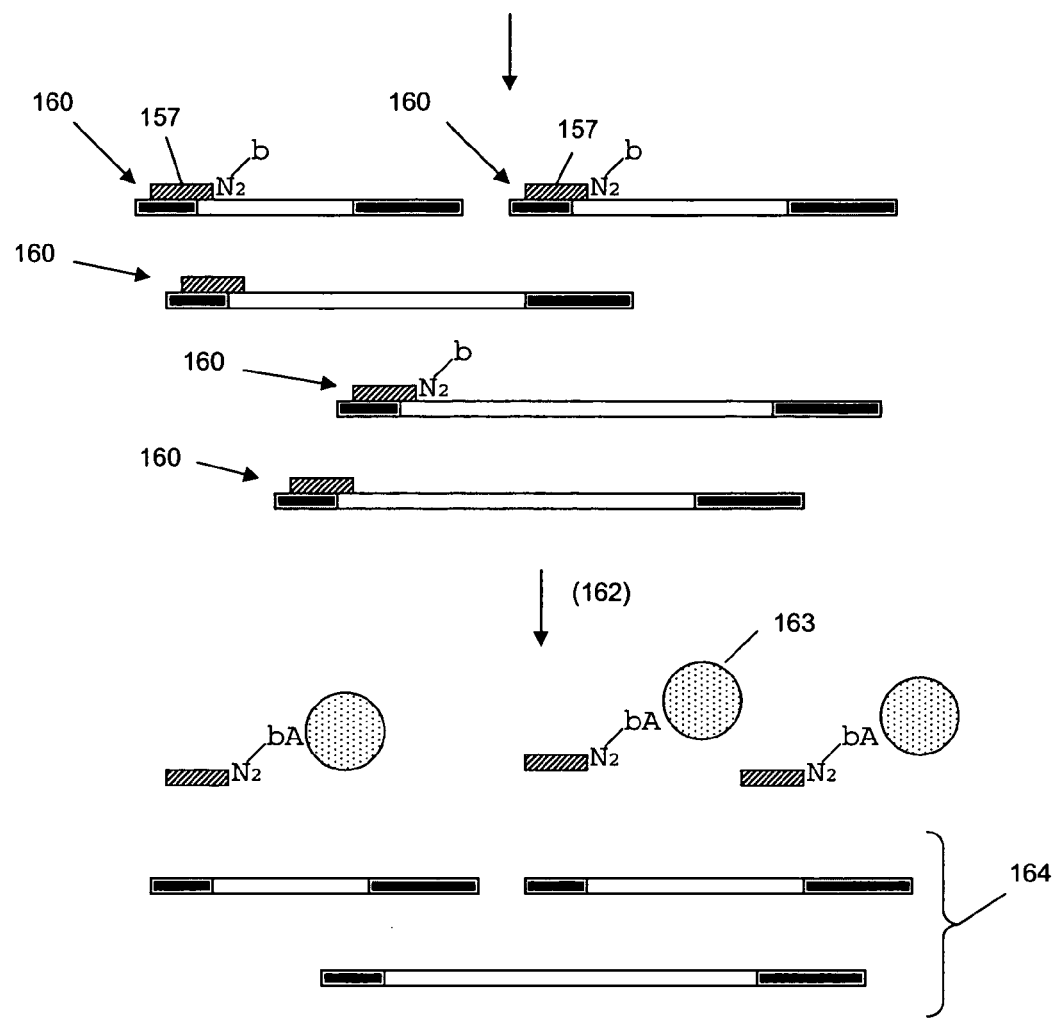

The invention also provides a method of carrying out successive selections using a set of overlapping primers of predetermined sequences to isolate a subset of polynucleotides having a common sequence, i.e. a predetermined sequence characteristic. By way of example, population (140) of FIG. 1D is formed by digesting a genome or large DNA fragment with one or more restriction endonucleases followed by the ligation of adaptors (142) and (144), e.g. as may be carried out in a conventional AFLP reactions, U.S. Pat. 6,045,994, which is incorporated herein by reference. Primers (149) are annealed (146) to polynucleotides (151) and extended, for example, by a DNA polymerase to incorporate biotinylated (150) dideoxynucleotide $N_1$ (148). After capture (152) with streptavidinated microbeads (120), selected polynucleotides are separated from primer-polynucleotide duplexes that were not extended (e.g. primer-polynucleotide duplex (147)) and melted to give population (154). Second primers (157) are selected so that when they anneal (156) they basepair with the first nucleotide of the template polynucleotide. That is, their sequence is selected so that they anneal to a binding site that is shifted (160) one base into the polynucleotide, or one base downstream, relative to the binding site of the previous primer. That is, in one embodiment, the three-prime most nucleotide of second primers (157) is $N_1$. In accordance with the invention, primers may be selected that have binding sites that are shifted downstream by more than one base, e.g. two bases. Second primers (157) are extended with a second terminator ("$N_2$-b" in FIG. 1E) and are captured by microbeads (163) having an appropriate capture agent to give selected population (164). Successive cycles of annealing primers, extension, capture, and melting (162) may be carried out with a set of primers that permits the isolation of a subpopulation of polynucleotides that all have the same sequence at a region adjacent to a predetermined restriction site. Preferably, after each cycle the selected polynucleotides are amplified to increase the quantity of material for subsequent reactions. In one aspect, amplification is carried out by a conventional linear amplification reaction using a primer that binds to one of the flanking adaptors and a high fidelity DNA polymerase. The number of amplification cycles may be in the range of from 1 to 10, and more preferably, in the range of from 4 to 8. Preferably, the same number of amplification cycles is carried out in each cycle of extension, capturing, and melting.

Figure 2A:
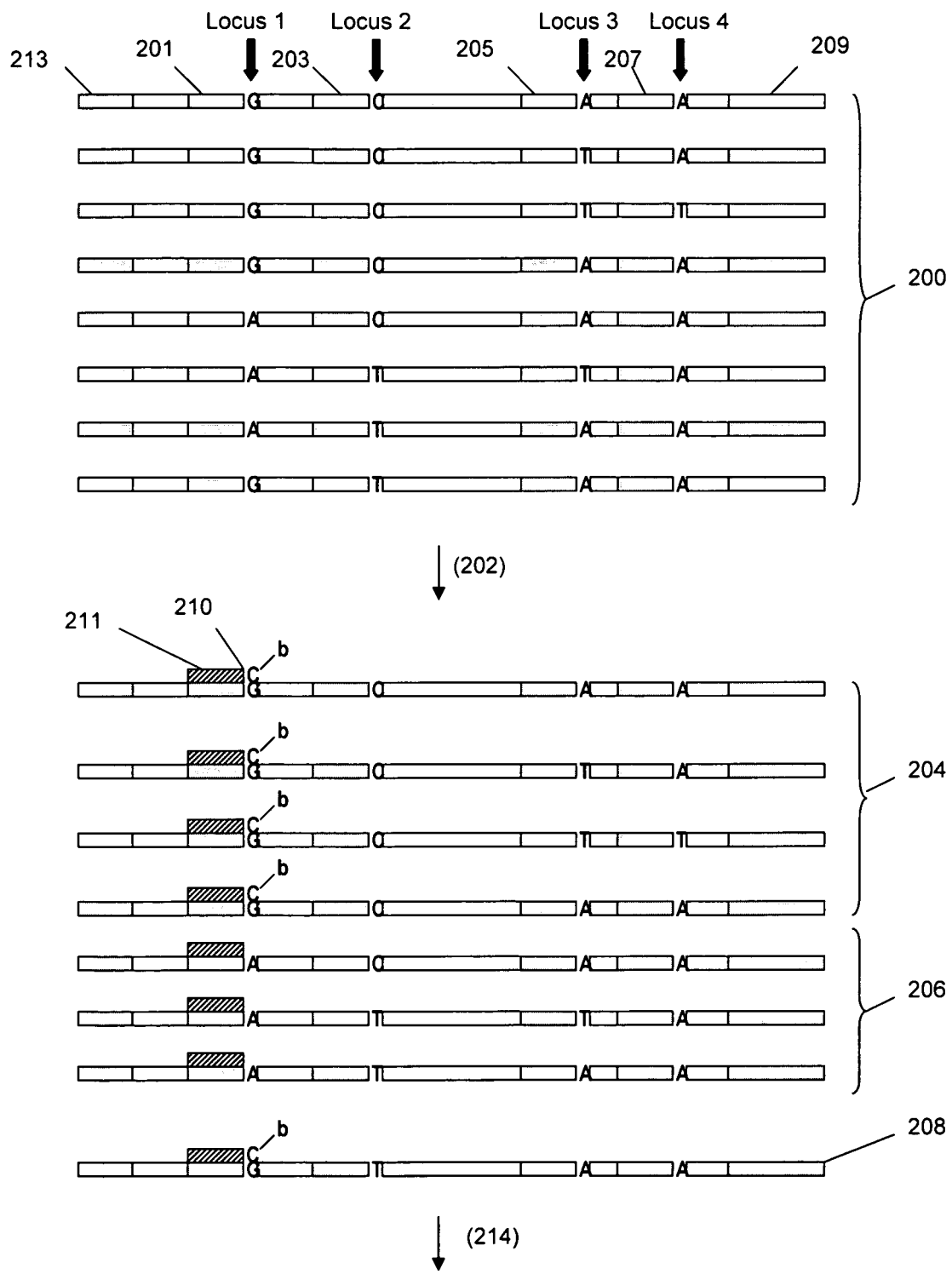
FIGS. 2A–2D illustrate the application of the invention for selecting particular haplotypes.
Figure 2B:
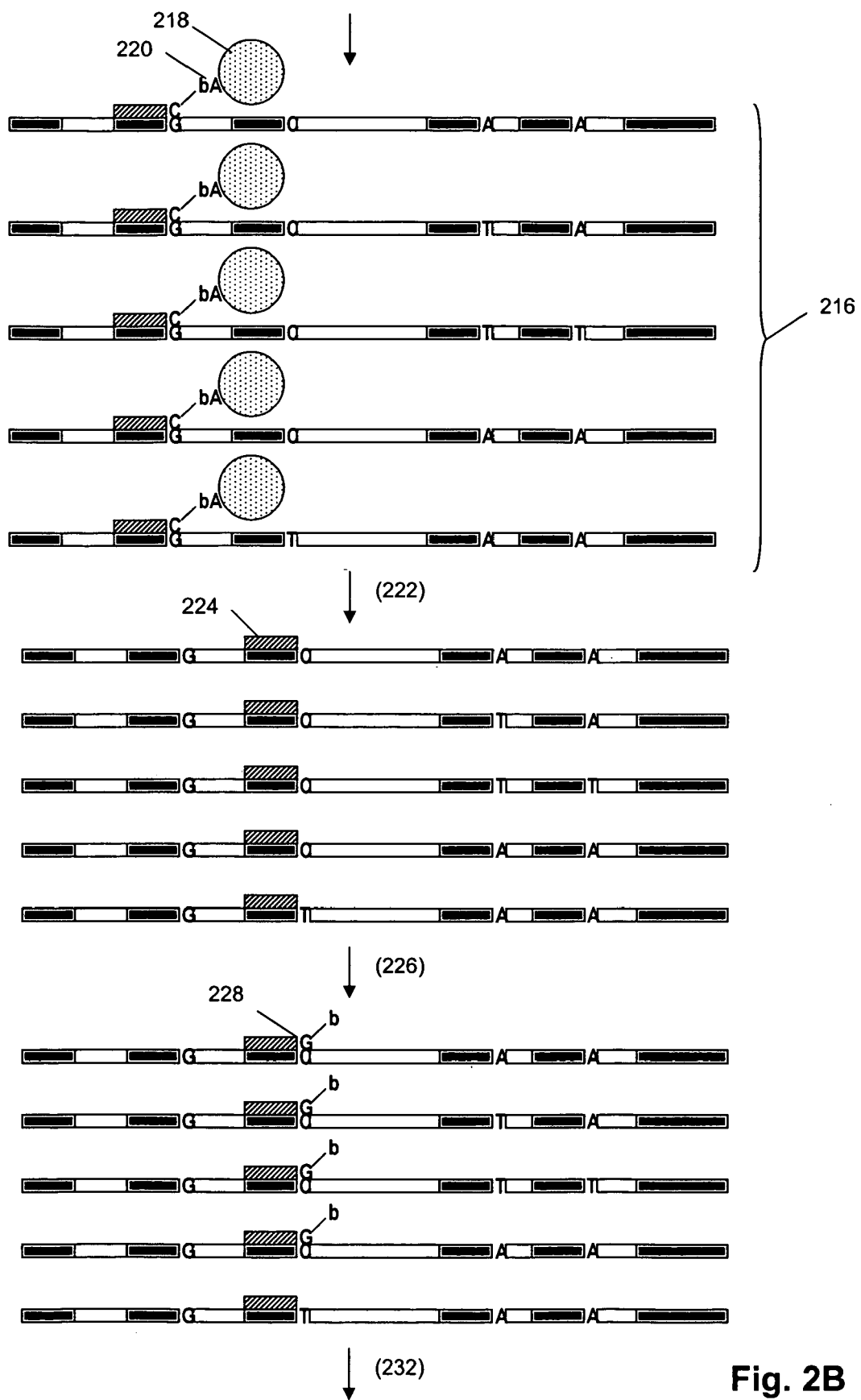
Figure 2C:
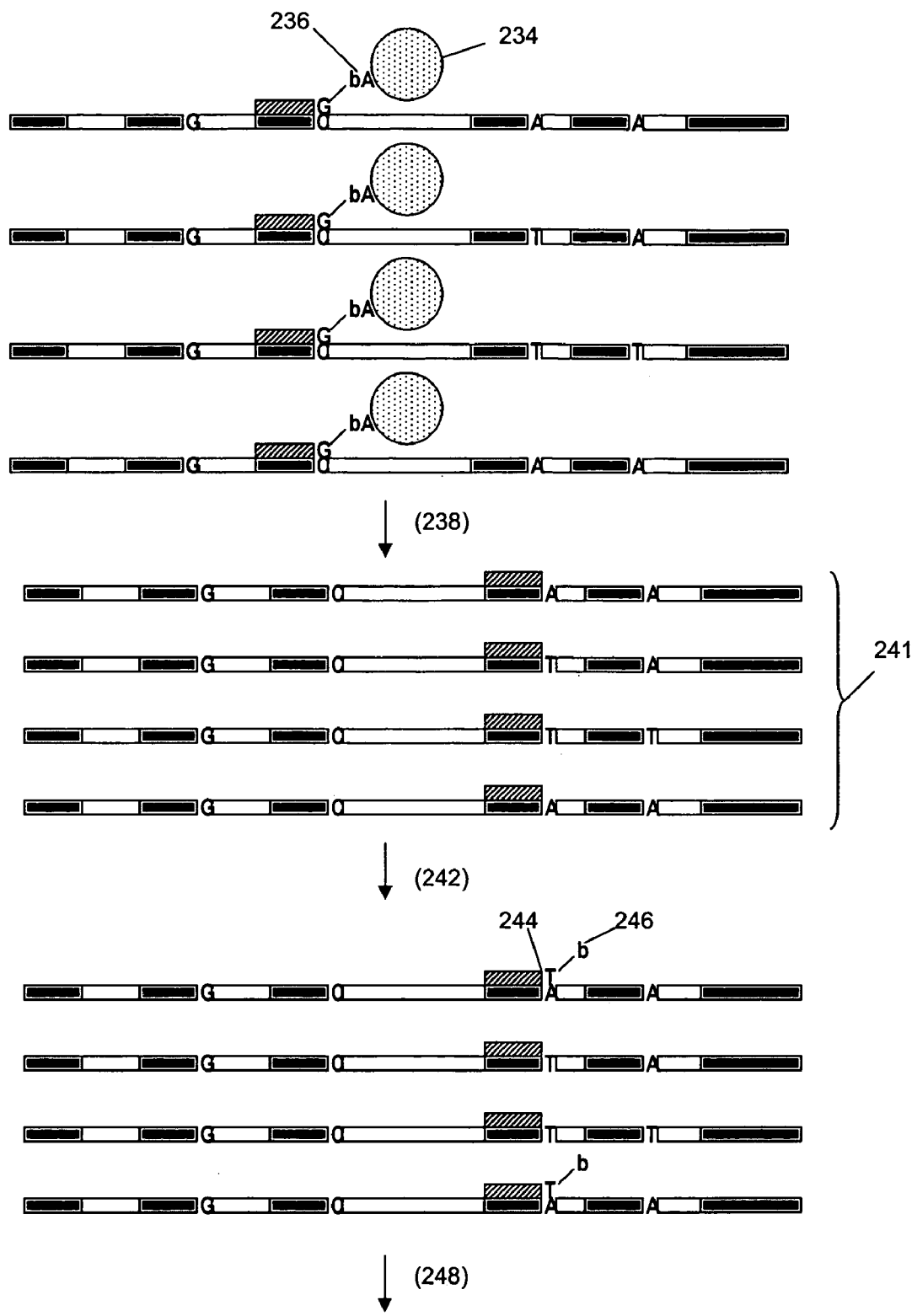
Figure 2D:
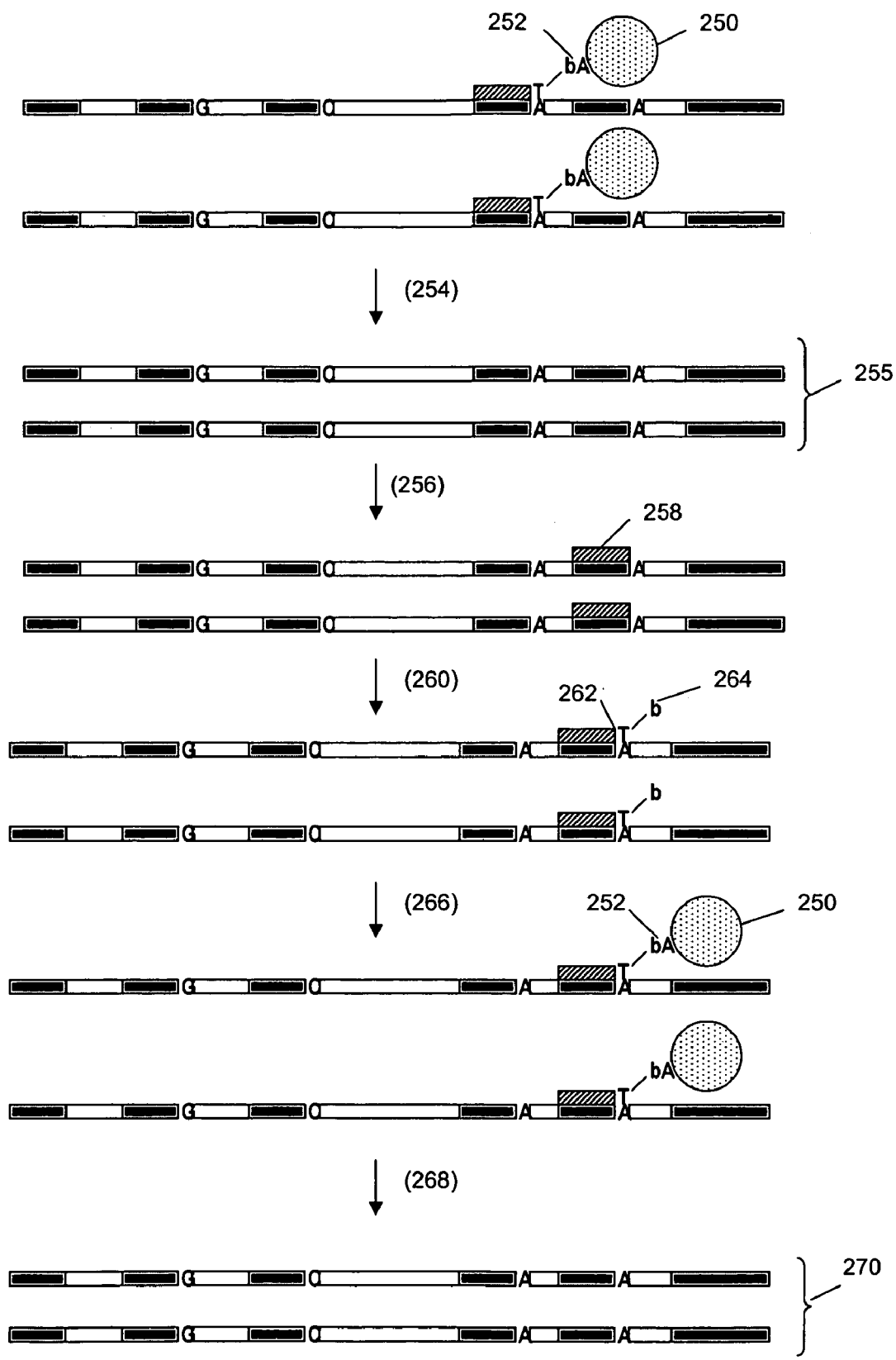

In another aspect, the invention includes a method for selecting a haplotype that comprises a sequence of SNPs adjacent to known sequence regions that are used as primer binding sites. For example, in FIG. 2A, population of polynucleotides (200) may correspond to restriction fragments of different genomes that contain polymorphic loci 1 through 4 adjacent to primer binding sites (201), (203), (205), and (207), respectively. Restriction fragments making up population (200) have adaptors (209) and (213) attached, which may be the same or different, unless oligonucleotide tags are attached to the fragments, as described more fully below. A haplotype is selected from the mixed population by successively selecting polynucleotides in accordance with the invention using primers that specifically anneal to sites (201), (203), (205), and (207). As illustrated, primer (211) anneals (202) to primer binding site (201) and is extended with a biotinylated dideoxycytidine terminator (210) since polynucleotides with a "G" at locus 1 are desired. Consequently, sequences (204) and (208) are selected (214) as described above using a solid phase support (218) having a capture agent (220). The selected polynucleotides (216) are melted and the next primer (224) is annealed (222) to binding site (203). Primers (224) are extended (226) with a biotinylated dideoxyguanosine terminator (228), because the next SNP of the desired haplotype is deoxycytidine. Solid phase supports (234) having capture agents (236) are added (232) to the reaction so that the extended primers together with their respective polynucleotides are selected. The process steps are repeated ((238), (242), (248), (254); and (256), (260), (266), (268)) for remaining loci producing successively less complex populations (241 and 255, respectively) until the polynucleotides containing the desired haplotype (270) is finally selected (where, as above. (244) is an incorporated terminator having capture moiety (246), (252) is a capture agent attached to solid phase support (250), (258) is an annealed primer, and (262) is an incorporated terminator having capture moiety (264))

Figure 1F:
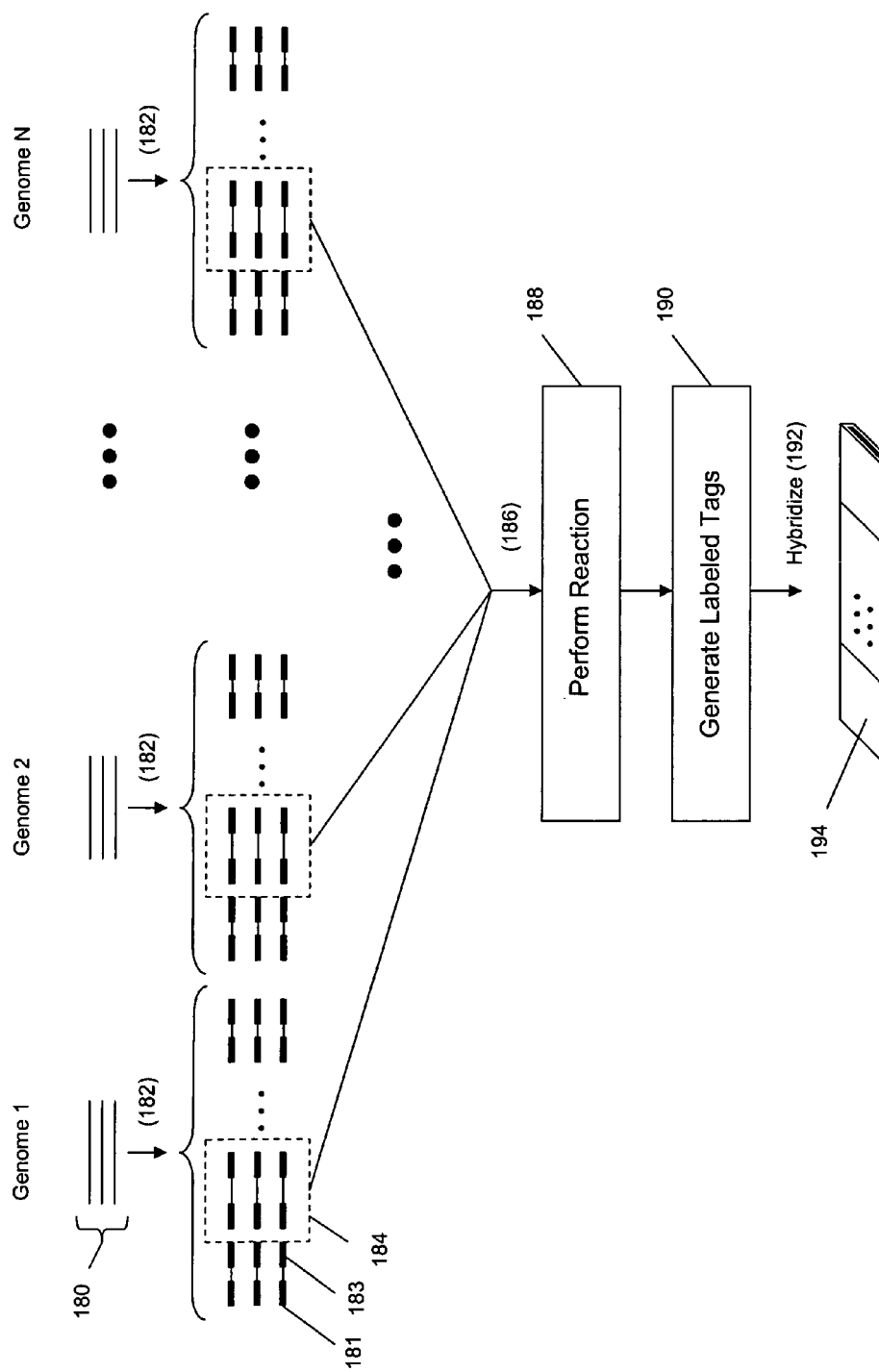

The selection methods described above may be used in another aspect of the invention in which the population of polynucleotides comprises genomes with unique tags. This aspect is illustrated in FIG. 1F. Genomes 1 through N are separately fragmented (182), e.g. in a conventional restriction endonuclease reaction, to produce fragments (180) to which adaptors (181 and 183) of the invention are attached. One of adaptors (181 or 183), examples of which are given below, contains a tag synthesized in accordance with the invention, and both adaptors (181 and 183) contain other sequences, such as primer binding sites and restriction sites, necessary to manipulate the fragments, as described above, for example. Using the sequence-specific sorting method of the invention, fragments (184) from a predetermined locus from each of the genomes are selected and combined (186) to form a reaction mixture. In other embodiments, fragments with adaptors (181 and 183) may be combined prior to selection. The isolated fragments in the reaction mixture may be analyzed (188) by a variety of techniques to identify SNPs or haplotypes, or the like, after which labeled tags are generated (190) to convey information obtained by the analytical reaction to a readout device, which preferably comprises the hybridization (192) of the labeled tags to a microarray (194), or like device. Microarray (194) contains at individual hybridization sites tag complements for every tag used to label the genomic fragments. Thus, if the analytical reaction employed identifies a nucleotide at a specific locus, i.e. a SNP, in each one of the N genomes, the SNP frequency at that locus in the population of genomes is simultaneously determined.

Virtually any population of polynucleotides may be analyzed by the method of the invention, including restriction digests, libraries of genomic fragments, cDNAs, mRNAs, or the like. Preferably, populations of polynucleotides analyzed by the invention are genomes of organisms whose sequences are known. Such genomes may be from any organism, including plant, animal, bacteria, or the like. When genomic DNA is obtained for medical or diagnostic use, it may be obtained from a wide variety of sources, including tissue biopsies, blood samples, amniotic cells, and the like. Genomic DNA is extracted from such tissues by conventional techniques, e.g. as disclosed in Berger and Kimmel, Editors, Methods in Enzymology, Vol. 152, Guide to Molecular Cloning Techniques (Academic Press, New York, 1987), or the like.

Hybridization Tags

An important feature of the invention is the use of hybridization tags consisting of oligonucleotides selected from a minimally cross-hybridizing set of oligonucleotides, or assembled from oligonucleotide subunits, i.e. "words," selected from a minimally cross-hybridizing set of oligonucleotides. Construction of such minimally cross-hybridizing sets are disclosed in Brenner et al, U.S. Pat. No. 5,846,719, and Brenner et al, Proc. Natl. Acad. Sci., 97: 1665–1670 (2000), which references are incorporated by reference. In accordance with Brenner, the sequences of oligonucleotides of a minimally cross-hybridizing set differ from the sequences of every other member of the same set by at least two nucleotides. Thus, each member of such a set cannot form a duplex (or triplex) with the complement of any other member with less than two mismatches. Preferably, perfectly matched duplexes of tags and tag complements of the same minimally cross-hybridizing set have approximately the same stability, especially as measured by melting temperature and/or dissociation temperature. Complements of hybridization tags, referred to herein as "tag complements," may comprise natural nucleotides or non-natural nucleotide analogs. Hybridization tags when used with their corresponding tag complements provide a means of enhancing the specificity, or discrimination, of hybridization. As used herein, the term minimally cross-hybridizing set also includes sets of 2-mers and 3-mers whose members differ from one another by at least a single nucleotide.

Minimally cross-hybridizing sets of oligonucleotide tags and tag complements may be synthesized either combinatorially or individually depending on the size of the set desired and the degree to which cross-hybridization is sought to be minimized (or stated another way, the degree to which specificity is sought to be enhanced). For example, a minimally cross-hybridizing set may consist of a set of individually synthesized 10-mer sequences that differ from each other by at least 4 nucleotides, such set having a maximum size of 332, when constructed as disclosed in Brenner et al, International patent application PCT/US96/09513. Alternatively, a minimally cross-hybridizing set of oligonucleotide tags may also be assembled combinatorially from subunits which themselves are selected from a minimally cross-hybridizing set. For example, a set of minimally cross-hybridizing 12-mers differing from one another by at least three nucleotides may be synthesized by assembling 3 subunits selected from a set of minimally cross-hybridizing 4-mers that each differ from one another by three nucleotides. Such an embodiment gives a maximally sized set of $9^3$, or 729, 12-mers.

When synthesized combinatorially, a hybridization tag preferably consists of a plurality of subunits, each subunit consisting of an oligonucleotide of 2 to 10 nucleotides in length wherein each subunit is selected from the same minimally cross-hybridizing set. In such embodiments, the number of hybridization tags available depends on the number of subunits per tag and on the length of the subunits.

Comma-Less Hybridization Tags

In one aspect of the invention, oligonucleotide tags are hybridized to their complementary sequences, or "anti-tags," which are attached to a solid phase support, such as a microarray. In such circumstances, it is desirable to employ oligonucleotide tags that are highly specific for anti-tags that form perfectly matched duplexes between each and every word of the tag, and that form, at best, only weakly stable duplexes with anti-tags in which words are not perfectly aligned. That is, in order to avoid spurious signals, it is desirable select sets of words (and tags constructed from them) that do not form stable duplexes when hybridized in an imperfectly aligned configuration, e.g. shifted 1 to 2, or more, bases out of perfect alignment. Sets of words with such properties may be constructed in several ways, including by inserting "commas" between words or by using words that inherently possess the above properties, i.e. which result in so-called "comma-less" tags, as discussed below. Tags of word having commas are readily constructed from the minimally cross-hybridizing sets of words disclosed by Brenner in the several references cited above. Either comma-containing or comma-less tags may be used with the invention; however, comma-less tags are preferred, as they generate the maximum degree of instability in a duplex formed after any small (e.g. 1–3 nucleotide) shift of the tag and anti-tag out of perfect alignment, also sometimes referred to herein as a "change of phase."

Figure 3A:
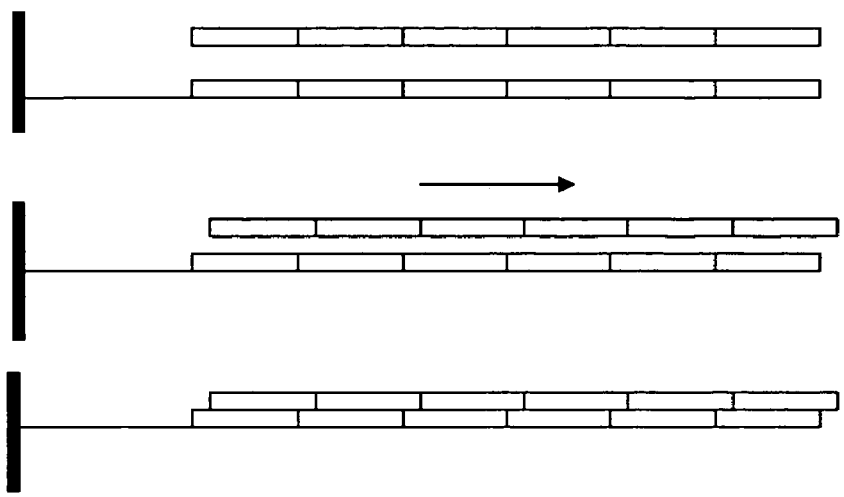
FIGS. 3A–3D illustrate hybridization tags with "commas" and a hybridization tag with the "comma-less" property.

As mentioned above, in tags synthesized combinatorially from shorter oligonucleotide "words," stable duplexes may form between a tag and its complement, even though the "words" are not perfectly aligned. As illustrated in FIG. 3A, an oligonucleotide tag consisting of words may align perfectly with its complement to form a perfectly matched duplex. However, with some selections of words, there may be other tags in the same repertoire that also form stable duplexes, even though the tag is shifted, or out of alignment, by one or more bases with a complement. The stability of such spurious pairings is very close to that of the perfectly aligned pairings, making it difficult to discriminate between correctly hybridized tags and incorrectly hybridized tags.

Figure 3B:
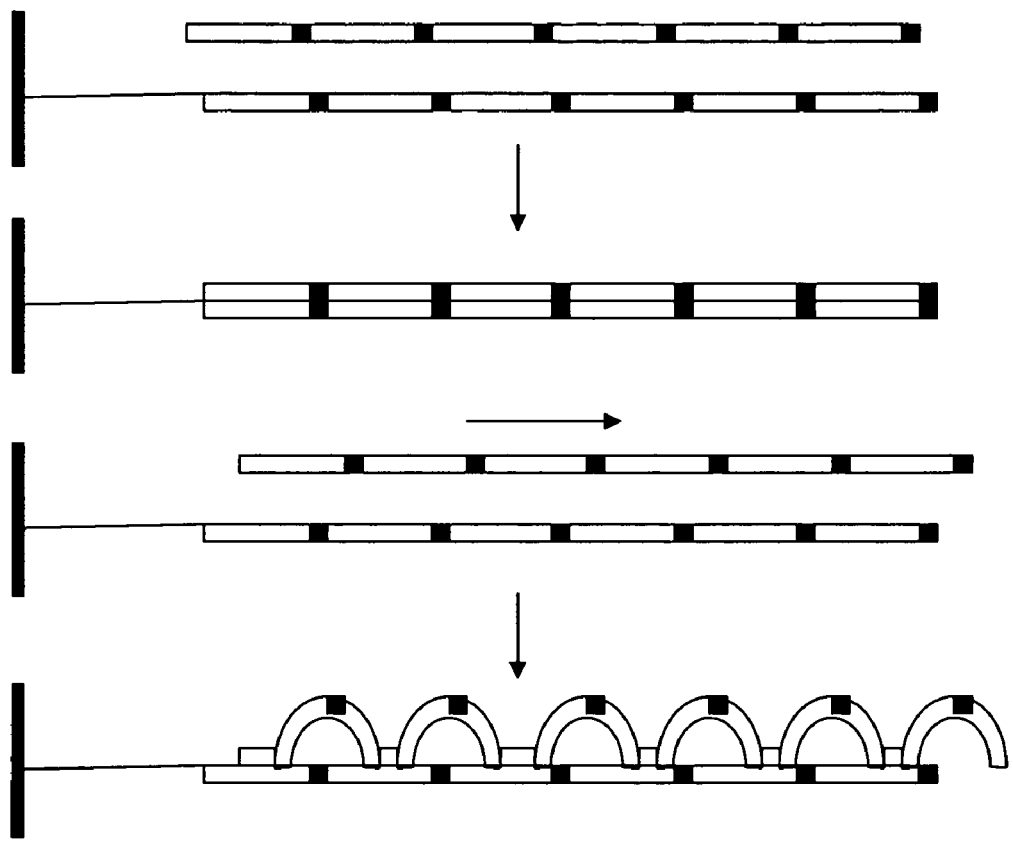

Such spurious hybridizations can be eliminated by designing tags that have large numbers of mismatches whenever the tag and its complement are shifted one or more bases away from the perfectly aligned configuration. As mentioned above, such designs can be accomplished by either introducing "commas" between words, or by designing words that inherently have the property that any shift out of perfect alignment introduces large numbers of stability-destroying mismatches. In its simplest form, "commas" may be one or more nucleotides introduced between the words of a tag, as illustrated in FIG. 3B. For example, the commas of a tag may consist of G's, while the words may consist of only A's, T's, and C's. Thus, for a perfectly matched duplex to form (i) the commas must be aligned, and (ii) the words of a tag must each be the complement of the words of its anti-tag. If neither of these conditions is met, then no duplex will form, or if it does form its stability will be vastly lower than that of the perfectly aligned and matched tags.

Figure 3C:
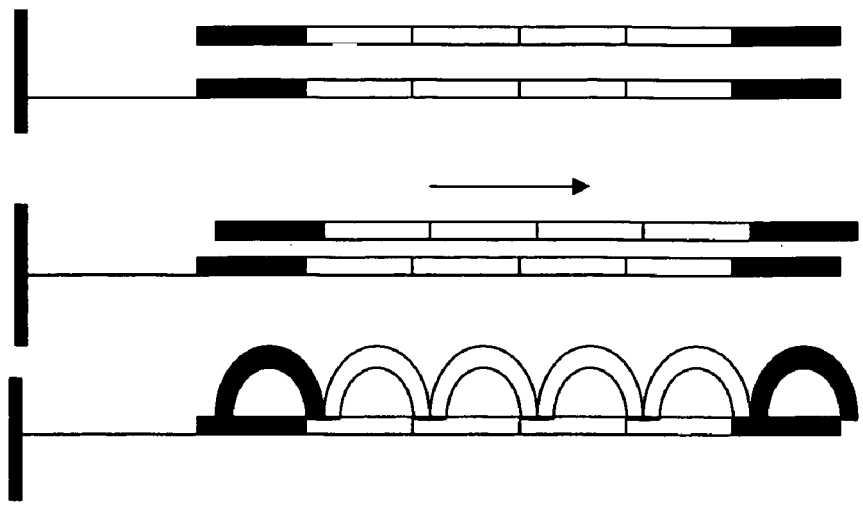

"Commas" may also take the form of words, as illustrated in FIG. 3C. Again, by way of example, the end words (shown in black) may consist of G's, whereas the internal words (shown in white) may consist of A's, C's, and T's. This constrains a tag and its complement to be correctly aligned. As above, absence perfect alignment, the stability of any duplex that forms will be vastly lower than that of a perfectly aligned tag and its complement.

Figure 3D:
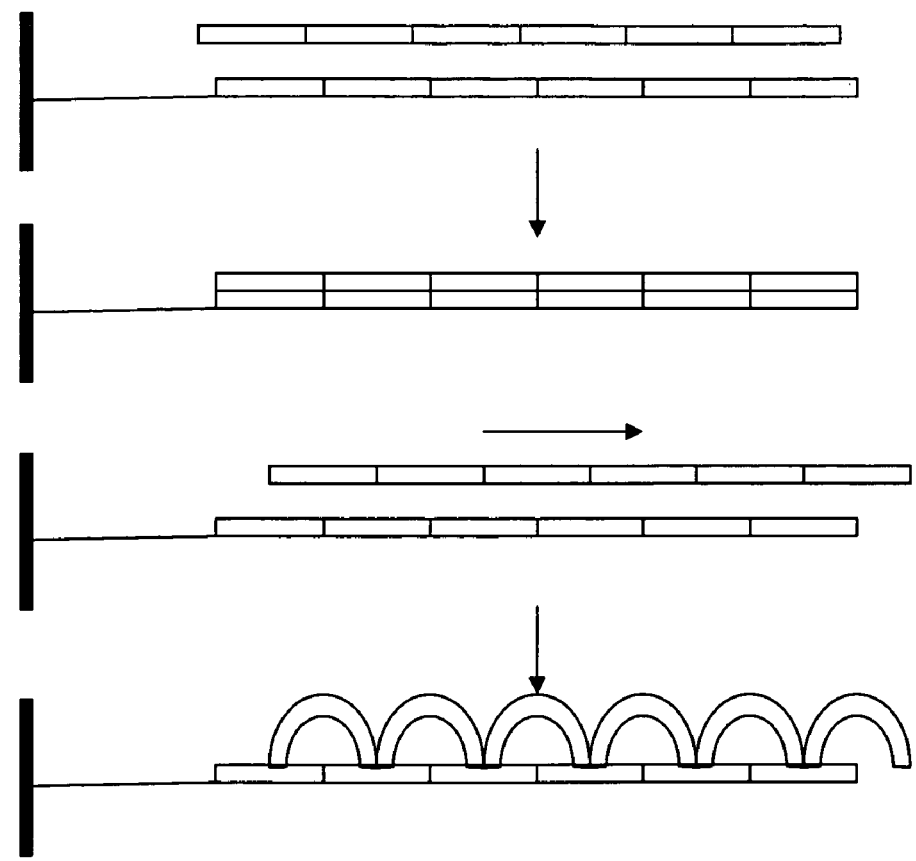

Finally, repertoires of tags without commas may be constructed from words that have the same properties as tags with commas. Such tags with the "comma-less" property are illustrated in FIG. 3D. That is, in order to form a perfectly matched duplex between a tag and a complement, the two must be perfectly aligned. Words for a repertoire of comma-less tags may be constructed in a wide variety of lengths, e.g. such words may have lengths in the range of from 4 to 10 nucleotides, and may consist of natural or non-natural nucleotides. In one aspect, words are construct from the four natural nucleotides, A, C, G, and T, whenever the resulting tags are operated on by enzymes. In another aspect, words may be constructed from nucleotides selected from the group consisting of A, C, G, T, and I, when the resulting tags (or anti-tags) are not processed by enzymes. Anti-tags synthesized on a solid phase support may typically be constructed from a wider variety of nucleotides than tags that are processed by enzymes. In one aspect of the invention, comma-less tags may be constructed from the following words.

Consider doublets of the four natural bases. Four sets of such doublets, 16 in all, can be defined as follows.

| I | II | III | IV |
|---|----|-----|----|
| GT | CT | AT | AA |
| TG | TC | TA | TT |
| AC | AG | CG | CC |
| CA | GA | GC | GG |

In each set, all four differ in both positions from all the other members of the set, but when the four different sets are compared with each other, one base is held in common with one member of the other set. For example, in set I, eight different words can be created by combining doublets from set I with doublets from set II in the I-II order and the II-I order. Since each of these sets contain doublets that are the reverse complements of the other, the combinations are made such that none of I-II four-base words are the inverse complements of the II-I four-base words. Thus, if the I-II words are selected as follows: GTCT, TGTC, ACAG, and CAGA, then the II-I words can be defined only as follows:

| AGCA | or | AGGT |
| GAAC |    | GATG |
| CTTG |    | CTAC |
| TCGT |    | TCCA | an arrangement which conserves the constraint that the members of each set differs by three bases from any member of the same set. From the above sets, several sets of words for comma-less tags can be constructed. Taking the first two sets, an "A" to the end of each words of the first set, and a "T" to the end of each word of the second set to give the following:

| AGCAT | GTCTA |
| GAACT | TGTCA |
| CTTGT | ACAGA |
| TCGTT | CAGAA |

Although the same process does not work with sets II and IV above because in III the doublets are self-complementary, further sets of words can be created by switching the I-II into II-I and vice versa, and adding the bases as above, which gives:

| | |
|---|---|
| CTGTA | CAAGT |
| TCTGA | ACGAT |
| AGACA | TGCTT |
| GACAA | GTTCT |

For tags not used in enzymatic processing, such as anti-tags synthesized on a solid phase support, the following sets employing deoxyinosine may be employed:

| | |
|---|---|
| AICAT | GTCTA |
| GAACT | TGTCA |
| CTTGT | ACAGA |
| TCITT and | CAGAA |
| CTGTA | CAAGT |
| TCTGA | ACIAT |
| AGACA | TICTT |
| GACAA | GTTCT |

Further sets of words for constructing comma-less tags are listed in FIG. 4.

Tag Complements Hybridization and Readout

Preferably, tag complements are synthesized on the surface of a solid phase support, such as a microscopic bead or a specific location on an array of synthesis locations on a single support, such that populations of identical, or substantially identical, sequences are produced in specific regions. That is, the surface of each support, in the case of a bead, or of each region, in the case of an array, is derivatized by copies of only one type of tag complement having a particular sequence. The population of such beads or regions contains a repertoire of tag complements each with distinct sequences. As used herein in reference to hybridization tags, tag complements, and synthesis tags, the term "repertoire" means the total number of different tags or tag complements in a given set or population.

Solid phase supports containing tag complements may take a variety of forms, e.g. particulate, single-piece and planar, such as a glass slide, and may be composed of a variety of materials, e.g. glass, plastic, silicon, polystyrene, or the like. Particulate solid phase supports include microspheres, particularly fluorescently labeled microspheres, e.g. Han et al, Nature Biotechnology, 19: 631–635 (2001); Kettman et al, Cytometry, 33: 234–243 (1998); and the like. Preferably, hybridization tags are detected by hybridizing them to their complementary sequences on a conventional microarray. Such microarrays may be manufactured by several alternative techniques, such as photo-lithographic optical methods, e.g. Pirrung et al, U.S. Pat. No. 5,143,854, Fodor et al, U.S. Pat. Nos. 5,800,992; 5,445,934; and 5,744,305; fluid channel-delivery methods, e.g. Southern et al, Nucleic Acids Research, 20: 1675–1678 and 1679–1684 (1992); Matson et al, U.S. Pat. No. 5,429,807, and Coassin et al, U.S. Pat. Nos. 5,583,211 and 5,554,501; spotting methods using functionalized oligonucleotides, e.g. Ghosh et al, U.S. Pat. No. 5,663,242; and Bahl et al, U.S. Pat. No. 5,215,882; droplet delivery methods, e.g. Caren et al, U.S. Pat. No. 6,323,043; Hughes et al, Nature Biotechnology, 19: 342–347 (2001); and the like. The above patents disclosing the synthesis of spatially addressable microarrays of oligonucleotides are hereby incorporated by reference.

Microarrays used with the invention contain from 50 to 500,000 hybridization sites; or from 100 to 250,000 hybridization sites; or from 100 to 40,000 hybridization sites; and preferably, they contain from 100 to 32,000 hybridization sites; or from 100 to 20,000 hybridization sites; or from 100 to 10,000 hybridization sites.

Guidance for selecting conditions and materials for applying labeled oligonucleotide probes to microarrays may be found in the literature, e.g. Wetmur, Crit. Rev. Biochem. Mol. Biol., 26: 227–259 (1991); DeRisi et al, Science, 278: 680–686 (1997); Wang et al, Science, 280: 1077–1082 (1998); Duggan et al, Nature Genetics, 21: 10–14 (1999); Schena, Editor, Microarrays: A Practical Approach (IRL Press, Washington, 2000); Hughes et al (cited above); Fan et al, Genomics Research, 10: 853–860 (2000); and like references. These references are hereby incorporated by reference. Typically, application of hybridization tags to a solid phase support includes three steps: treatment with a pre-hybridization buffer, treatment with a hybridization buffer that includes the probes, and washing under stringent conditions. A pre-hybridization step is employed to suppress potential sites for non-specific binding of probe. Preferably, pre-hybridization and hybridization buffers have a salt concentration of between about 0.8–1.2 M and a pH between about 7.0 and 8.3. Preferably, a pre-hybridization buffer comprises one or more blocking agents such as Denhardt's solution, heparin, fragmented denature salmon sperm DNA, bovine serum albumin (BSA), SDS or other detergent, and the like. An exemplary pre-hybridization buffer comprises 6×SSC (or 6×SSPE), 5× Denhardt's solution, 0.5% SDS, and 100 µg/ml denatured, fragmented salmon sperm DNA, or an equivalent defined-sequence nucleic acid. Another exemplary pre-hybridization buffer comprises 6×-SSPE-T (0.9 M NaCl, 60 mM NaH2PO4, 6 mM EDTA (pH 7.4), 0.005% Triton X-100) and 0.5 mg/ml BSA. Pre-hybridization and hybridization buffers may also contain organic solvents, such as formamide to control stringency, tetramethylammonium chloride to negate base-specific effects, and the like. An exemplary hybridization buffer is SSPE-T and the desired concentration of isostringency probe. After hybridization, unbound and non-specifically bound isostringency probe is removed by washing the detection support under stringent conditions. Preferably, stringency of the wash solution is controlled by temperature, organic solvent concentration, or salt concentration. More preferably, the stringency of the wash conditions are determined to be about 2–5° C. below the melting temperature of the isostringency probes at the salt concentration and pH of the wash solution. Preferably, the salt concentration of the wash solution is between about 0.01 to 0.1 M.

Instruments for measuring optical signals, especially fluorescent signals, from labeled tags hybridized to targets on a microarray are described in the following references which are incorporated by reference: Stern et al, PCT publication WO 95/22058; Resnick et al, U.S. Pat. No. 4,125,828; Kamaukhov et al, U.S. Pat. No. ,354,114; Trulson et al, U.S. Pat. No. 5,578,832; Pallas et al, PCT publication WO 98/53300; Brenner et al, Nature Biotechnology, 18: 630–634 (2000); and the like.

When tag complements are attached to or synthesized on microbeads, a wide variety of solid phase materials may be used with the invention, including microbeads made of controlled pore glass (CPG), highly cross-linked polystyrene, acrylic copolymers, cellulose, nylon, dextran, latex, polyacrolein, and the like, disclosed in the following exemplary references: Meth. Enzymol., Section A, pages 11–147, vol. 44 (Academic Press, New York, 1976); U.S. Pat. Nos. 4,678,814; 4,413,070; and 4,046;720; and Pon, Chapter 19, in Agrawal, editor, Methods in Molecular Biology, Vol. 20, (Humana Press, Totowa, N.J., 1993). Microbead supports further include commercially available nucleoside-derivatized CPG and polystyrene beads (e.g. available from Applied Biosystems, Foster City, Calif.); derivatized magnetic beads; polystyrene grafted with polyethylene glycol (e.g., TentaGel™, Rapp Polymere, Tubingen Germany); and the like. Generally, the size and shape of a microbead is not critical; however, microbeads in the size range of a few, e.g. 1–2, to several hundred, e.g. 200–1000 μm diameter are preferable, as they facilitate the construction and manipulation of large repertoires of oligonucleotide tags with minimal reagent and sample usage. Preferably, glycidal methacrylate (GMA) beads available from Bangs Laboratories (Carmel, Ind.) are used as microbeads in the invention. Such microbeads are useful in a variety of sizes and are available with a variety of linkage groups for synthesizing tags and/or tag complements.

Hybridization Code

In one aspect, hybridization codes of the invention consist of five bases and are assembled into hybridization tags following a procedure similar to that described in Brenner and Williams (cited above). Using synthesis tags, hybridization tags are constructed that are complements of the anti-tags attached to solid phase supports, such as microarrays. Such tags have the following form (SEQ ID NO: 9):

```
. . . GCATCNNNNN-H₁-H₂-NNNNNNNNNCATCC . . .        (I)
      Sfa NI                    Fok I
``` where $H_1$ and $H_2$ are words of a hybridization tag as described above, for example 4-mer words. Such words may vary in length depending on the embodiment, but generally are in the range of from 2 to 10 nucleotides in length; or they may be in the range of from 3 to 6 nucleotides in length. One factor in selecting word length is whether they are processed by restriction enzymes, such as type IIs restriction enzymes, whose recognition and cleavage characteristics may dictate word length. Using an eight-word set described above, 64 such di-words are constructed, cloned in conventional vectors, and the DNA can be obtained thereafter by PCR. These reagents containing pairs of hybridization "words" are used to form word-pair conversion adaptors, described more fully below.

The principle of successively adding words is as follows. Assuming a word is in place and that a successive word is to be added. Since the previous word can be any of the eight words, then the material to be added will need to have all possibilities in the next position, call this "$H_2$", and there would be eight such sets. Thus, when the Sfa NI site is cut we will have the following end:

$$pZ_1Z_1Z_1Z_1\ Z_1Z_0Z_0Z_0Z_0Z_0 \ldots \quad (II)$$

$$Z_1Z_0Z_0Z_0Z_0Z_0 \ldots$$

where the "$Z_1$'s" are the nucleotides of the added word, the "$Z_0$'s" are the nucleotides of the previous word, and "p" is a phosphate group. The new word is added by cutting the di-words of formula (I) at the Fok I site to give (SEQ ID NO: 10):

$$\ldots GCATCNNNNN-Z_2Z_2Z_2Z_2Z_2Z_2Z_2$$

$$\ldots CGTAGNNNNN-Z_2Z_2Z_2Z_2Z_2Z_2Z_2Z_xZ_xZ_xZ_xp$$

where the "$Z_2$'s" are the nucleotides of the next word, and the "$Z_x$'s" are the nucleotides of all the possible cleavage products. The cleavage product includes ends complementary to all of the possible ends of the cleavage product of formula (II). Thus, ligation of the two products permits combinatorial synthesis of the tags.

Tagging Polynucleotides

In one aspect of the invention, all fragments of each genome of a population of genomes are labeled with one combination of words selected from a repertoire of 32,768 ($=8^5$) five-word oligonucleotide tags. Once each genome has a unique tag, then common-sequence fragments, e.g. a restriction fragment from a particular locus, can be selected using the method of the invention. The tags may then be used to convey information about the fragments, e.g. the identity of a nucleotide at a particular locus, to a hybridization array for a readout. One of ordinary skill in the art understands that the selection of 5-word oligonucleotide tags of five nucleotides each and the use of commaless tags are design choices that may be varied depending on the goals and constraints of any particular application. In one embodiment the following eight-word minimally cross-hydridizing set may be used to construct the above repertoire. As described below, preferably, each word is cloned in a plasmid with additional elements for aiding in the construction of oligonucleotide tags.

| | |
|---|---|
| AGCAT | GTCTA |
| GAACT | TGACA |
| TCTGT | ACGAA |
| CTGTT | CATCA |

Using these words, 64 di-words are prepared in separate plasmids as described in Brenner and Williams (cited above), which is incorporated by reference.

A. Single-Word Library and Counting Array Element.

In one embodiment, the single word library contains a ten-base sequence [G/T; G/T; A/T]₃G/T, where "x/T" is an equal mixture of the two bases "x" and "T" at a particular locus. This element encodes a repertoire of 1024 ($=2^{10}$) different sequences that permits sequences to be counted by hybridization of copies of the sequence to an array of complementary sequences, i.e. a "counting" array. This element is referred to herein as the "Counting Array" or "CAR" element. In this embodiment, about 30 copies of each genome are tagged and each is labeled with one unique sequence. Thus, if any sorted molecule is found to have a unique sequence for this array, it is not a genome difference that should have multiple sequences, and is likely to represent an error in the process which has resulted in an altered molecule. Note that however much any fragment is amplified that it will always possess the original sequences in the counting array, preserving cardinality as distinct from the concentration of DNA.

A plasmid having the following characteristics is constructed: (i) no SapI site, and (ii) a sequence of restriction sites:

```
     GGGCCC . . . AGGCCT . . . GGTACC
     (ApaI)       (BspE1)      (KpnI)
```

These sites each have "GG" which is absent from tags constructed from the words of the above set. Next for each word the strands of following element are synthesized (SEQ ID NO: 11):

```
5'-pCNNNNNNNNNNNGCATCNNNNNN [WORD] A
3'-CCGGGNNNNNNNNNNCGTAGNNNNN [WORD] TCCGGp
              (Sfa N1)
``` where lower case "p" represents a phosphate group. After annealing the strands, the element is cloned into the above plasmid by cleaving with ApaI and Bsp E1. Several plasmids are picked for each word and the clones are sequenced to check the accuracy of the sequence, after which one is selected for use in tag construction. Elements for the "counting" array are synthesized and also a second primer binding site which will be required for later amplification. After synthesis, the following structure is obtained (SEQ ID NO: 12):

```
3'-NNNTCCGGA [N15] CCCTG [(G/T;G/T;A/T)3G/T]
     BspE1         BsmF1      CAR element GTTGCTTCTCGCCATGGNNNN
                              SapI      KpnI
```

Using the primer "5'-NNNAGGCCT[N15]GGGAC" (SEQ ID NO: 13) the above is copied, cleaved with KpnI and BspE1, and cloned into each of the single-word plasmids. 10 clones of each are isolated to make sure that all the sequences of the counting array are in the library.

This embodiment is designed to attach tags to fragments generated by cleaving with the "↓GATC" family of restriction endonucleases. These enzymes permit the generation of the fragments of several different lengths:

| Enzyme | Recognition Site | Average Fragment Length |
|---|---|---|
| Bam HI | G↓GATCC | 4 Kb |
| Bam HI + BglII | G↓GATCC + G↓GATCT | 2 Kb |
| Bst YI | R↓GATCY | 1 Kb |
| Sau 3a | ↓GATC | 256 bp |

All of these leave the same end when cleaved, namely:

```
5'-NN

NNCTAGp
``` where "p" is a phosphate group. This may be filled in with a single dGTP to give a three-base overhang:

```
5'-NNG

NNCTAGp
```

After such filling, polynucleotides or cloning vectors cut with SapI (underlined below), which leaves the following ends:

```
5'- . . . NN      GATCGAAGAGC . . .

. . . NNTAGp      GCTTCTCG . . .
``` permits efficient and directional cloning of fragments.

The final construct has the following structure:

```
. . . [ApaI site]N10[SfaN1 site]N5[word][BspE1 site]N15[BsmF1 site][CAR][SapI site][KpnI site] . . .
        Primer X                         Primer Y                              Primer Z
``` were "N" are arbitrarily selected nucleotides and "CAR" is a counting array element, as described above.

B. Double-Word Libraries.

Here a library of 64 vectors is disclosed each containing one of the 64 possible two-word, or "di-word," concatenations of words from the 8-word library flanked by primer binding sites. This double-word library is then used essentially as described in Brenner and Williams (cited above) to construct oligonucleotide tags. In this embodiment, the first flanking primer binding site is that shown above as "Primer X," and the other contains a recognition site for FokI, 5'-GGATG(9/13), which contains "GG" and therefore cannot cut any of the words described above.

The following vector elements are synthesized (SEQ ID NO: 14):

```
5'-pCN10[SfaN1 site]N5[word 1][word 2]N8CATCC
``` and (SEQ ID NO: 15):

```
3'-CCGGGN10[SfaN1 site]N5[word 1][word 2]
                                           N9GTAGGCTAG
``` where it is understood that the "word 1" and "word 2" refer to both word sequences and their respective complements. After annealing the above fragments to form a doublestranded element, it is cloned into a plasmid digested with ApaI and BamHI. To assure the accuracy of the incorporation, several clones of each "double word" vector are selected and sequenced. Copies of di-words may be conveniently obtained by PCR using a biotinylated X primer and another primer.

C. Tagging Genomes.

About 1 ng of human DNA (about 300 copies of the haploid genome) is digested with Bst Y1 to give fragments of an average size of 1 Kb, after which ends are filled in with dGTP to give 3-base ends as described above.

The eight single word libraries, labeled A–H, are amplified and cut with SapI to generate the following single-word fragment:

```
[ApaI site]N10[SfaN1 site]N5[word][BspE1 site]N15[BsmF1 site][CAR]

[ApaI site]N10[SfaN1 site]N5[word][BspE1 site]N15[BsmF1 site][CAR]CTAp
   Primer X                               Primer Y
```

64 genomes are tagged in one batch as follows. 64 reaction vessels are arranged in an 8×8 array wherein each row, 1–8, contains 8 vessels labeled A–H. To each vessel a different Bst YI-digested genome is added, after which a different single-word fragment, A–H, is added to vessels 1–8, in each row to give the following array of reaction vessels with the following single-word fragments:

| Row | Single-Word Fragment | | | | | | | |
|---|---|---|---|---|---|---|---|---|
| 1 | A | B | C | D | E | F | G | H |
| 2 | A | B | C | D | E | F | G | H |
| 3 | A | B | C | D | E | F | G | H |
| 4 | A | B | C | D | E | F | G | H |
| 5 | A | B | C | D | E | F | G | H |
| 6 | A | B | C | D | E | F | G | H |
| 7 | A | B | C | D | E | F | G | H |
| 8 | A | B | C | D | E | F | G | H |

The single-word fragments are ligated to the genome fragments to give genome fragments having single-word fragments on both ends. These fragments are processed as follows so that a single-word fragment is on only one end. First, the reaction constituents from every vessel in each row are pooled so that eight mixed samples are obtained.

| Row | Single-Word Fragment |
|---|---|
| 1 | A + B + C + D + E + F + G + H |
| 2 | A + B + C + D + E + F + G + H |
| 3 | A + B + C + D + E + F + G + H |
| 4 | A + B + C + D + E + F + G + H |
| 5 | A + B + C + D + E + F + G + H |
| 6 | A + B + C + D + E + F + G + H |
| 7 | A + B + C + D + E + F + G + H |
| 8 | A + B + C + D + E + F + G + H |

The DNA of each of the eight vessels is denatured and Primer Y (pAGGCCTN$_{15}$GGGAC) (SEQ ID NO: 16) is added to prime the 3' tag sequence of each of the single strands as follows (SEQ ID NO: 17 AND SEQ ID NOL 18):

```
AGGCCTN15GGGAC

TCCGGAN15CCCTG[CAR]CTAG[fragment]CTAG[CAR]
                                       GTCCC . . .
```

The primer is extended using 5-Me-dCTP to give the following (SEQ ID NO: 19 AND SEQ ID NO: 20):

```
AGGCCTN15GGGAC[CAR]GATC(Me)  [fragment]GATC(Me)
[CAR]GTC(Me)C(Me)C(Me) . . .

TCCGGAN15CCCTG[CAR]CTAG       [fragment]CTAG
              [CAR]CAG       G           G    . . .
```

All of the BsmF1 sites of the fragments are protected by half methylation, except for the site to the left of the tag. When the fragments are cleaved with BsmF1, the lefthand tag is removed up to the "GATC" site, leaving the following (SEQ ID NO: 21):

```
                          ↓
         . . . GGGAC[CAR]GATC[fragment] . . .
         . . . CCCTG[CAR]CTAG[fragment] . . .
                          ↑
                          ↓
GATC[fragment]GATC[CAR][BsmF1 site][Primer Y][word]N5[SfaN1 site][Primer X]
    [fragment]CTAG[CAR][BsmF1 site][Primer Y][word]N5[SfaN1 site][Primer X]
```

The "GATC" overhang is filled in with dGTP and ligated to the following adaptor containing a primer binding site for sequencing (SEQ ID NO: 22):

```
N20GC^Me   ATCAG

N20CG      TAGTCTAGp
```

The methylated C in the upper strand protects the lefthand site while the right hand portion of the fragments are manipulated. Words are added as follows. First, the C's of the bottom strand are replaced with 5-methyl-C's. This is accomplished by denaturing the above fragments, priming with a biotinylated Primer X (5'-biotin-GGGCCCN$_{10}$[Sfa N1 site]N$_5$), copying with 5-Me-CTP, and removing the strands with avidinated support. The fragments are released by cleaving with Sfa N1 to give in each of the eight vessels the sequences:

[fragment]GATC[CAR][Primer Y]W

-continued

[fragment]CTAG[CAR][Primer Y]WWWWWp where all eight words are represented in the overhang and "W" represents a nucleotide of a word or its complement. Next the di-word libraries are pooled, cleaved with FokI, then ligated to the above fragment to add the next word. The process is continued until the desired number of words is added to the genomic fragments to complete the tags.

I claim:

1. A method of sorting polynucleotides having predetermined sequence characteristics to form a subpopulation of reduced complexity, the method comprising the steps of:
   extending a primer annealed to polynucleotides having predetermined sequence characteristics to incorporate a predetermined terminator having a capture moiety;
   capturing polynucleotides having an extended primer by a capture agent that specifically binds to the capture moiety;
   melting the captured polynucleotides from the extended primer; and
   isolating the melted polynucleotides; thereby recovering an isolated subpopulation of reduced complexity.

2. A method of producing a subpopulation of polynucleotides having a complexity less than that of a parent population, the method comprising the steps of:
   annealing a primer to polynucleotides of a parent population to form primer-polynucleotide duplexes;
   extending the primer to incorporate a predetermined terminator having a capture moiety;
   separating the primer-polynucleotide duplexes having an extended primer from the parent population by specifically binding the capture moiety of the predetermined terminator to a capture agent attached to a solid phase support; and
   melting the primer-polynucleotide duplexes, thereby recovering an isolated subpopulation of polynucleotides having a complexity less than that of the parent population.

3. A method of producing a population of polynucleotides having a desired complexity less than that of a parent population, the method comprising the steps of:
   (a) annealing a primer to polynucleotides of a parent population to form primer-polynucleotide duplexes;
   (b) extending the primer to incorporate a predetermined terminator having a capture moiety;
   (c) separating the primer-polynucleotide duplexes having an extended primer from the parent population by specifically binding the capture moiety of the predetermined terminator to a capture agent attached to a solid phase support;
   (d) melting the polynucleotides from the primer-polynucleotide duplexes attached to the solid phase support, thereby recovering a selected population of polynucleotides having a complexity less than that of the parent population, the selected population forming a parent population for subsequent steps; and (e) repeating steps (a) through (d) until a selected population of the desired complexity is obtained.

4. The method of claim 3 further comprising a step of replicating said selected population after said step of melting.

5. The method of claim 4 wherein during each said step of repeating steps (a) through (d), said primer anneals to a different primer binding site on said polynucleotides of said parent population or said selected population.

6. The method of claim 5 wherein in each successive step of repeating steps (a) through (d), said different primer binding site is shifted along said polynucleotides at least one nucleotide in a primer extension direction.

7. The method of claim 5 wherein in each successive step of repeating steps (a) through (d), said different primer binding site is at a different and non-overlapping locus of said polynucleotides.

8. The method of claim 7 wherein said different and non-overlapping locus is adjacent to and upstream of a single nucleotide polymorphism site.

* * * * *

UNITED STATES PATENT AND TRADEMARK OFFICE
CERTIFICATE OF CORRECTION

| | | |
|---|---|---|
| PATENT NO. | : 7,217,522 B2 | Page 1 of 1 |
| APPLICATION NO. | : 11/055187 | |
| DATED | : May 15, 2007 | |
| INVENTOR(S) | : Sydney Brenner et al. | |

It is certified that error appears in the above-identified patent and that said Letters Patent is hereby corrected as shown below:

On the title page of the patent under the Assignee field please make the following correction:

Delete "Campass Genetics LLC" and replace with --Compass Genetics LLC--

Signed and Sealed this

Eighteenth Day of September, 2007

JON W. DUDAS
*Director of the United States Patent and Trademark Office*

SEQUENCE LISTING

<160> NUMBER OF SEQ ID NOS: 22

<210> SEQ ID NO 1
<211> LENGTH: 15
<212> TYPE: DNA
<213> ORGANISM: Unknown
<220> FEATURE:
<223> OTHER INFORMATION: Probe

<400> SEQUENCE: 1
agtctactgg tttca                                                    15

<210> SEQ ID NO 2
<211> LENGTH: 23
<212> TYPE: DNA
<213> ORGANISM: Unknown
<220> FEATURE:
<223> OTHER INFORMATION: Probe

<400> SEQUENCE: 2
gggttggggt ttaccccttt agc                                           23

<210> SEQ ID NO 3
<211> LENGTH: 20
<212> TYPE: DNA
<213> ORGANISM: Unknown
<220> FEATURE:
<223> OTHER INFORMATION: Adaptor

<400> SEQUENCE: 3
tattagctta cttggcctta                                               20

<210> SEQ ID NO 4
<211> LENGTH: 26
<212> TYPE: DNA
<213> ORGANISM: Unknown
<220> FEATURE:
<223> OTHER INFORMATION: Probe

<400> SEQUENCE: 4
agtctactgg tttcaattaa ttaatt                                        26

<210> SEQ ID NO 5
<211> LENGTH: 23
<212> TYPE: DNA
<213> ORGANISM: Unknown
<220> FEATURE:
<223> OTHER INFORMATION: Probe

<400> SEQUENCE: 5
gggttggggt ttaccccttt agc                                           23

```
<210> SEQ ID NO 6
<211> LENGTH: 15
<212> TYPE: DNA
<213> ORGANISM: Unknown
<220> FEATURE:
<223> OTHER INFORMATION: Probe

<400> SEQUENCE: 6
tcagatgacc aaagt                                                         15

<210> SEQ ID NO 7
<211> LENGTH: 30
<212> TYPE: DNA
<213> ORGANISM: Unknown
<220> FEATURE:
<223> OTHER INFORMATION: Probe

<400> SEQUENCE: 7
tcagatgacc aaagttcaga tgaccaaagt                                         30

<210> SEQ ID NO 8
<211> LENGTH: 10
<212> TYPE: DNA
<213> ORGANISM: Unknown
<220> FEATURE:
<223> OTHER INFORMATION: Probe

<400> SEQUENCE: 8
cccttagctg                                                               10

<210> SEQ ID NO 9
<211> LENGTH: 31
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: (6)..(26)
<223> OTHER INFORMATION: n is a, c, g, or t

<400> SEQUENCE: 9
gcatcnnnnn nnnnnnnnnn nnnnnncatc c                                       31

<210> SEQ ID NO 10
<211> LENGTH: 16
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: (6)..(16)
<223> OTHER INFORMATION: n is a, c, g, or t

<400> SEQUENCE: 10
gcatcnnnnn nnnnnn                                                        16

<210> SEQ ID NO 11
<211> LENGTH: 26
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: (2)..(11)
<223> OTHER INFORMATION: n is a, c, g, or t
```

```
<220> FEATURE:
<221> NAME/KEY: misc_feature
<222> LOCATION: (17)..(25)
<223> OTHER INFORMATION: n is a, c, g, or t

<400> SEQUENCE: 11
cnnnnnnnnn ngcatcnnnn nnnnna                                                26

<210> SEQ ID NO 12
<211> LENGTH: 65
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (37)..(56)
<223> OTHER INFORMATION: n is a, c, g, or t
<220> FEATURE:
<221> NAME/KEY: misc_feature
<222> LOCATION: (63)..(65)
<223> OTHER INFORMATION: n is a, c, g, or t

<400> SEQUENCE: 12
nnnnggtacc gctcttcgtt gkdddddddd dgtcccnnnn nnnnnnnnnn nnnnnnaggc           60 ctnnn                                                                      65

<210> SEQ ID NO 13
<211> LENGTH: 29
<212> TYPE: DNA
<213> ORGANISM: Unknown
<220> FEATURE:
<223> OTHER INFORMATION: Primer
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(24)
<223> OTHER INFORMATION: n is a, c, g, or t

<400> SEQUENCE: 13
nnnaggcctn nnnnnnnnnn nnnngggac                                            29

<210> SEQ ID NO 14
<211> LENGTH: 42
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: (2)..(11)
<223> OTHER INFORMATION: n is a, c, g, or t
<220> FEATURE:
<221> NAME/KEY: misc_feature
<222> LOCATION: (17)..(37)
<223> OTHER INFORMATION: n is a, c, g, or t

<400> SEQUENCE: 14
cnnnnnnnnn ngcatcnnnn nnnnnnnnnn nnnnnnncat cc                             42

<210> SEQ ID NO 15
<211> LENGTH: 51
<212> TYPE: DNA
```

<213> ORGANISM: Unknown
<220> FEATURE:
<223> OTHER INFORMATION: Adaptor
<220> FEATURE:
<221> NAME/KEY: misc_feature
<222> LOCATION: (10)..(31)
<223> OTHER INFORMATION: n is a, c, g, or t
<220> FEATURE:
<221> NAME/KEY: misc_feature
<222> LOCATION: (37)..(46)
<223> OTHER INFORMATION: n is a, c, g, or t

<400> SEQUENCE: 15
gatcggatgn nnnnnnnnnn nnnnnnnnnn nctacgnnnn nnnnnngggc c     51

<210> SEQ ID NO 16
<211> LENGTH: 26
<212> TYPE: DNA
<213> ORGANISM: Unknown
<220> FEATURE:
<223> OTHER INFORMATION: Primer
<220> FEATURE:
<221> NAME/KEY: misc_feature
<222> LOCATION: (7)..(21)
<223> OTHER INFORMATION: n is a, c, g, or t

<400> SEQUENCE: 16
aggcctnnnn nnnnnnnnnn ngggac     26

<210> SEQ ID NO 17
<211> LENGTH: 19
<212> TYPE: DNA
<213> ORGANISM: Unknown
<220> FEATURE:
<223> OTHER INFORMATION: Adaptor

<400> SEQUENCE: 17
ccctgkdddd dddddgatc     19

<210> SEQ ID NO 18
<211> LENGTH: 40
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: (20)..(34)
<223> OTHER INFORMATION: n is a, c, g, or t

<400> SEQUENCE: 18
gatckddddd ddddgtcccn nnnnnnnnnn nnnnaggcct     40

<210> SEQ ID NO 19
<211> LENGTH: 40
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: (7)..(21)
<223> OTHER INFORMATION: n is a, c, g, or t
<220> FEATURE:
<221> NAME/KEY: 5-methylcytosine
<222> LOCATION: (40)..(40)

<400> SEQUENCE: 19
aggcctnnnn nnnnnnnnnn ngggacdddd dddddkgatc     40

```
<210> SEQ ID NO 20
<211> LENGTH: 19
<212> TYPE: DNA
<213> ORGANISM: Unknown
<220> FEATURE:
<223> OTHER INFORMATION: Adaptor
<220> FEATURE:
<221> NAME/KEY: 5-methylcytosine
<222> LOCATION: (4)..(4)
<220> FEATURE:
<221> NAME/KEY: 5-methylcytosine
<222> LOCATION: (17)..(19)

<400> SEQUENCE: 20
gatcdddddd dddkgtccc                                                19

<210> SEQ ID NO 21
<211> LENGTH: 19
<212> TYPE: DNA
<213> ORGANISM: Unknown
<220> FEATURE:
<223> OTHER INFORMATION: Adaptor

<400> SEQUENCE: 21
gggacddddd ddddkgatc                                                19

<210> SEQ ID NO 22
<211> LENGTH: 27
<212> TYPE: DNA
<213> ORGANISM: Unknown
<220> FEATURE:
<223> OTHER INFORMATION: Adaptor
<220> FEATURE:
<221> NAME/KEY: misc_feature
<222> LOCATION: (1)..(20)
<223> OTHER INFORMATION: n is a, c, g, or t
<220> FEATURE:
<221> NAME/KEY: 5-methylcytosine
<222> LOCATION: (22)..(22)

<400> SEQUENCE: 22
nnnnnnnnnn nnnnnnnnnn gcatcag                                       27
```